(12) United States Patent
Sokoloff et al.

(10) Patent No.: US 9,217,145 B2
(45) Date of Patent: Dec. 22, 2015

(54) T7 PHAGE PEPTIDE DISPLAY SYSTEM AND USES THEREOF

(75) Inventors: Alexander V. Sokoloff, Madison, WI (US); Jon Asher Wolff, Shorewood, WI (US); James John Ludtke, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1620 days.

(21) Appl. No.: 12/121,176

(22) Filed: May 15, 2008

(65) Prior Publication Data

US 2009/0113562 A1    Apr. 30, 2009

Related U.S. Application Data

(60) Provisional application No. 60/938,110, filed on May 15, 2007.

(51) Int. Cl.
*A01K 67/027* (2006.01)
*C12N 15/00* (2006.01)
*C12Q 1/70* (2006.01)
*C12N 15/10* (2006.01)
*C07K 14/005* (2006.01)

(52) U.S. Cl.
CPC .......... *C12N 15/1037* (2013.01); *C07K 14/005* (2013.01); *C12N 2795/10222* (2013.01)

(58) Field of Classification Search
None
See application file for complete search history.

(56) References Cited

PUBLICATIONS

Slootweg et al. (Nucleic Acids Reesearch, 2006 vol. 34 No. 20, e137, pp. 1-11).*

* cited by examiner

*Primary Examiner* — Robert A Zeman
(74) *Attorney, Agent, or Firm* — Kening Li; Miller Canfield

(57) ABSTRACT

A bacteriophage T7 display vector for expressing and displaying an exogenous peptide, wherein the display vector comprises a polynucleotide encoding a bacteriophage T7 tail fiber protein p17 in which a hepatocyte-targeting determinant sequence is inactivated, and wherein a cloning site is contained in a coding sequence for the tail fiber protein p17 or in a coding sequence for a capsid protein p10B. Also provided are a host cell containing the display vector as described above, a bacteriophage T7 particle comprising at least one copy of a p17 protein which comprises an exogenous peptide displayed thereon, or at least one copy of a p10 protein with an exogenous peptide displayed thereon, wherein a hepatocyte-targeting determinant sequence on the bacteriophage T7 tail fiber protein p17 is inactivated. The present invention further provides a viral lysate containing assembled bacteriophage T7 particle described above, and a method for determining if a candidate peptide is a liver-targeting peptide, or for screening for liver targeting peptides.

10 Claims, 6 Drawing Sheets

```
WT p10b     ADQIIAKYAMGHGGLRPEAAGAVVFQSGVMLGVASTVAASPEEASVTSTEETLTP
20-6        ADQIIAKYAMGHGGLRPEAAGAVVFQZ
```

Figure 6A

```
20-6    AATGAAGCCTTACAGTTCCGTAATGAGGCTGAGACTTTCAGAAACCAAGCGGAGGGCTTT
        ||||||||||||||||||| |||||||||||||||||||||||||||||||||||||||
lib     AATGAAGCCTTACAGTTCCGGAATGAGGCTGAGACTTTCAGAAACCAAGCGGAGGGCTTT 20-6    AAGAACGAGTCCAGTACCAACGCTACGAACACAAAGCAGTGGCGCGATGAGACCAAGGGT
        ||||||||||||||||  ||  ||||||||||||||||||||||||||||||||||||||
lib     AAGAACGAGTCCAGTACGAATTCTACGAACACAAAGCAGTGGCGCGATGAGACCAAGGGT 20-6    TTCCGAGACGAAGCCGAGCGGTTCAAGAATACGGCTGGTCAATACGCTACATCTGCTGGG
        ||||||||||||||||||||||||||||   |||||||||||||||||||||||||||||
lib     TTCCGAGACGAAGCCGAGCGGTTCAAGCTTACGGCTGGTCAATACGCTACATCTGCTGGG 20-6    AACTCTGCTTCCGCTGCGCATCAATCTGAGGTAAACGCTGAGAACTCTGCCACAGCATCC
        |||||||||||||| |||||||||||||||||||||||||||||||||||||||||||||
lib     AACTCTGCTTCCGCGGCGCATCAATCTGAGGTAAACGCTGAGAACTCTGCCACAGCATCC
```

Figure 6B p17 line ups: Top sequence is 20-6 sequence (the only difference from wild type is the highlighted and underlined G which is an A in the wild type sequence. Genetic changes to introduce cloning sites are highlighted in grey. The first T>G change introduces the BspEI site. The CAACG>GAATTC introduces the EcoRI site. The AA>CT introduces the HindIII site, and the T>G introduces the SacII site.

SEQUENCE LISTING

```
<160> NUMBER OF SEQ ID NOS: 99

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagtacttgg agcgtgcact ggacccaac                                            29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagtctcagc ctcattccgg aactgtaagg                                           30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccttacagtt ccggaatgag gctgagactt                                           30

<210> SEQ ID NO 4
<211> LENGTH: 29
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 4
ccatcagtgg ccacaacggc ctgacctac                                             29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagtacttgg agcgtgcact ggacccaac                                             29

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtttacctc agattgatgc gccgcggaag ca                                         32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcttccgcg gcgcatcaat ctgaggtaaa cg                                         32

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatcagtgg ccacaacggc ctgacctac                                             29

<210> SEQ ID NO 9
<211> LENGTH: 19
<212> TYPE: PRT
<213> ORGANISM: Homo sapiens

<400> SEQUENCE: 9

His Leu Arg Lys Leu Arg Lys Arg Leu Leu Arg Asp Ala Asp Asp Leu
 1               5                  10                  15

Gln Lys Arg

<210> SEQ ID NO 10
<211> LENGTH: 55
<212> TYPE: PRT
<213> ORGANISM: Enterobacteria phage T7

<400> SEQUENCE: 10

```
Ala Asp Gln Ile Ile Ala Lys Tyr Ala Met Gly His Gly Gly Leu Arg
  1               5                  10                  15

Pro Glu Ala Ala Gly Ala Val Val Phe Gln Ser Gly Val Met Leu Gly
             20                  25                  30

Val Ala Ser Thr Val Ala Ala Ser Pro Glu Glu Ala Ser Val Thr Ser
         35                  40                  45

Thr Glu Glu Thr Leu Thr Pro
     50                  55

<210> SEQ ID NO 11
<211> LENGTH: 27
<212> TYPE: PRT
<213> ORGANISM: Enterobacteria phage T7

<400> SEQUENCE: 11

Ala Asp Gln Ile Ile Ala Lys Tyr Ala Met Gly His Gly Gly Leu Arg
  1               5                  10                  15

Pro Glu Ala Ala Gly Ala Val Val Phe Gln Glx
             20                  25

<210> SEQ ID NO 12
<211> LENGTH: 240
<212> TYPE: DNA
<213> ORGANISM: Enterobacteria phage T7

<400> SEQUENCE: 12
aatgaagcct acagttccg taatgaggct gagactttca gaaaccaagc ggagggcttt      60
aagaacgagt ccagtaccaa cgctacgaac acaaagcagt ggcgcgatga gaccaagggt    120
ttccgagacg aagccgagcg gttcaagaat acggctggtc aatacgctac atctgctggg    180
aactctgctt ccgctgcgca tcaatctgag gtaaacgctg agaactctgc cacagcatcc    240

<210> SEQ ID NO 13
<211> LENGTH: 240
<212> TYPE: DNA
<213> ORGANISM: Enterobacteria phage T7

<400> SEQUENCE: 13
aatgaagcct acagttccg gaatgaggct gagactttca gaaaccaagc ggagggcttt      60
aagaacgagt ccagtacgaa ttctacgaac acaaagcagt ggcgcgatga gaccaagggt    120
ttccgagacg aagccgagcg gttcaagctt acggctggtc aatacgctac atctgctggg    180
aactctgctt ccgcggcgca tcaatctgag gtaaacgctg agaactctgc cacagcatcc    240

<210> SEQ ID NO 14
<211> LENGTH: 16
<212> TYPE: PRT
<213> ORGANISM: Homo sapiens

<400> SEQUENCE: 14

Leu Ser Val Lys Ala Gln Tyr Lys Lys Asn Lys His Arg His Ser Ile
  1               5                  10                  15

<210> SEQ ID NO 15
<211> LENGTH: 4
<212> TYPE: PRT
<213> ORGANISM: Enterobacteria phage T7

<400> SEQUENCE: 15

Val Val Phe Gln
```

<210> SEQ ID NO 16
<211> LENGTH: 18
<212> TYPE: PRT
<213> ORGANISM: Enterobacteria phage T7

<400> SEQUENCE: 16

Thr Asn Thr Lys Gln Trp Arg Asp Glu Thr Lys Gly Phe Arg Asp Glu
 1               5                  10                  15
Ala Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (17)
<223> OTHER INFORMATION: Any amino acid

<400> SEQUENCE: 17

Xaa Asn Thr Xaa Xaa Trp Arg Asp Glu Thr Xaa Xaa Phe Arg Xaa Glu
 1               5                  10                  15
Xaa

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Asn Thr Tyr Ala Trp Arg Asp Glu Thr Lys Lys Phe Arg Asn Glu
 1               5                  10                  15
Ser

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Asn Thr Leu Phe Trp Arg Asp Glu Thr Val Gly Phe Arg Asp Glu

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gly Asn Thr Tyr Gln Trp Arg Asp Glu Thr Gly Leu Phe Arg Asp Glu
1               5                   10                  15
Leu

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gln Asn Thr Leu Lys Trp Arg Asp Glu Thr Phe Asn Phe Arg His Glu
1               5                   10                  15
Glu

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Asp Asn Thr Tyr Arg Trp Arg Asp Glu Thr Ser Asn Phe Arg Thr Glu
1               5                   10                  15
Leu

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ser Asn Thr Thr Thr Trp Arg Asp Glu Thr Ser Thr Phe Arg Tyr Glu
1               5                   10                  15
Phe

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Val Asn Thr Lys Gly Trp Arg Asp Glu Thr Tyr Lys Phe Arg Glu Glu
 1               5                  10                  15
Ile

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Asn Thr Arg Ser Trp Arg Asp Glu Thr Glu Leu Phe Arg His Glu
 1               5                  10                  15
Phe

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Asn Thr Ile Lys Trp Arg Asp Glu Thr Phe Ile Phe Arg Glu Glu
 1               5                  10                  15
Val

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Asn Thr Arg Arg Trp Arg Asp Glu Thr Tyr Ile Phe Arg Thr Glu
 1               5                  10                  15
Ser

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Asn Thr Gln Glu Trp Arg Asp Glu Thr Tyr Phe Phe Arg Asp Glu
 1               5                  10                  15
Asn

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Leu Asn Thr Val Ile Trp Arg Asp Glu Thr Glu Gly Phe Arg Arg Glu
 1               5                  10                  15
Val
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Arg Asn Thr Trp Ala Trp Arg Asp Glu Thr Phe Asn Phe Arg Ser Glu
 1               5                  10                  15
Leu
```

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Ser Asn Thr His Glu Trp Arg Asp Glu Thr Leu Ala Phe Arg Val Glu
 1               5                  10                  15
Ser
```

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Glu Asn Thr Arg Leu Trp Arg Asp Glu Thr Tyr Lys Phe Arg Lys Glu
 1               5                  10                  15
Tyr
```

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Leu Asn Thr Arg Arg Trp Arg Asp Glu Thr Lys Ile Phe Arg Val Glu
 1               5                  10                  15
Glu
```

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 34

Gly Asn Thr Gln Lys Trp Arg Asp Glu Thr Leu Arg Phe Arg Tyr Glu
 1               5                  10                  15
Thr

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Asn Thr Arg Glu Trp Arg Asp Glu Thr Lys His Phe Arg Glu Glu
 1               5                  10                  15
Ile

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Asn Thr Asn Gln Trp Arg Asp Glu Thr Ile Arg Phe Arg Ser Glu
 1               5                  10                  15
Arg

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Asn Thr Arg Arg Trp Arg Asp Glu Thr Gln Thr Phe Arg Ile Glu
 1               5                  10                  15
Lys

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Thr Val His Trp Arg Asp Glu Thr Lys Arg Phe Arg Glu Glu
 1               5                  10                  15
Ile

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 39

Thr Asn Thr Lys Gln Trp Arg Asp Glu Thr Met Arg Phe Arg Lys Glu
 1               5                  10                  15
Ser

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Asn Thr Arg Ala Trp Arg Asp Glu Thr Asn Lys Phe Arg Ile Glu
 1               5                  10                  15
Lys

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Asn Thr Ala Thr Trp Arg Asp Glu Thr His His Phe Arg Ser Glu
 1               5                  10                  15
Lys

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Asn Thr Ser Arg Trp Arg Asp Glu Thr Lys His Phe Arg Ser Glu
 1               5                  10                  15
Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Asn Thr Arg Val Trp Arg Asp Glu Thr Leu Val Phe Arg Lys Glu
 1               5                  10                  15
Lys

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 44

Lys Asn Thr Thr His Trp Arg Asp Glu Thr Gln Asn Phe Arg Ser Glu
 1               5                  10                  15
Arg

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (11)..(18)
<223> OTHER INFORMATION: Any amino acid

<400> SEQUENCE: 45

Xaa Xaa Xaa Xaa Xaa Trp Arg Asp Glu Thr Xaa Xaa Xaa Xaa Xaa Xaa
 1               5                  10                  15
Xaa Xaa

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Asn Thr Ala Arg Trp Arg Asp Glu Thr Gln Thr Phe Arg Thr Glu
 1               5                  10                  15
Ala Arg

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Asn Thr Arg Val Trp Arg Asp Glu Thr Ser Thr Phe Arg Asn Glu
 1               5                  10                  15
Ala Arg

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Asn Thr Lys Arg Trp Arg Asp Glu Thr Thr Ser Phe Arg Gln Glu
 1               5                  10                  15

Ala Arg

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Asn Met Ser Arg Trp Arg Asp Glu Thr Ser Arg Leu Val Arg Arg
 1               5                  10                  15

Leu Glu

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Gln Met Glu Asn Trp Arg Asp Glu Thr Ser Arg Ala Ser Arg Arg
 1               5                  10                  15

Ser Leu

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Gln Met Glu Asn Trp Arg Asp Glu Thr Ser Arg Ala Ser Arg Arg
 1               5                  10                  15

Ser Leu

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Ile Arg Lys Trp Arg Asp Glu Thr Val Ile Leu Ser Lys Arg
 1               5                  10                  15

Ser Ser

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Arg Ile Gln Ala Trp Arg Asp Glu Thr Glu Ile Ser Ser Arg Arg
 1               5                  10                  15

Ser Ser

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Gln Met Gln Leu Trp Arg Asp Glu Thr Leu Leu Ser Arg Ser Arg
 1               5                  10                  15

Ser Leu

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Ala Ile Ala Leu Trp Arg Asp Glu Thr Ala Val Ser Arg Asn Lys
 1               5                  10                  15

Ser Leu

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Val Val Lys Gly Trp Arg Asp Glu Thr Tyr Glu Ser Arg Asp Lys
 1               5                  10                  15

Cys Arg

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Asn Thr Gly Arg Trp Arg Asp Glu Thr Lys Met Phe Arg Arg Glu
 1               5                  10                  15

Ala Met

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Asn Thr Gly Arg Trp Arg Asp Glu Thr Asp Ser Phe Arg Arg Glu

```
                1               5                  10                  15
Ala Arg

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Asn Thr Asn Lys Trp Arg Asp Glu Thr Thr Leu Phe Arg Arg Glu
1               5                   10                  15

Ala Arg

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Asn Thr Asn Met Trp Arg Asp Glu Thr Ser Arg Phe Arg Arg Glu
1               5                   10                  15

Ala Gly

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Asn Thr Asn Val Trp Arg Asp Glu Thr Gly Arg Phe Arg Lys Glu
1               5                   10                  15

Ala Leu

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Glu Val Arg Leu Trp Arg Asp Glu Thr Ile Pro Val Leu Arg Arg
1               5                   10                  15

Ile Leu

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

Arg Lys Ser Glu Met Trp Arg Asp Glu Thr Ala Ala Asn Tyr Arg Arg
 1               5                   10                  15

Ile Ser

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Gly Val Asn Leu Trp Arg Asp Glu Thr Ser Arg Asn Cys Lys Arg
 1               5                   10                  15

Ala Leu

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Leu Ile Ser Arg Trp Arg Asp Glu Thr Asn Leu Leu Tyr Lys Arg
 1               5                   10                  15

Gln His

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Gly Ile His Gly Trp Arg Asp Glu Thr Leu Gly Ala Leu Lys Arg
 1               5                   10                  15

Val Val

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala His Cys Arg Thr Trp Arg Asp Glu Thr Gln Lys Thr Thr Glu Arg
 1               5                   10                  15

Leu Arg

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Glu Gly Ile Arg Thr Trp Arg Asp Glu Thr Ala Val Ala Ser Val Arg
 1               5                  10                  15

Ala Arg

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Gln Val Ser Thr Trp Arg Asp Glu Thr Ile Val Ser Thr Thr Arg
 1               5                  10                  15

Thr Arg

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Gly Val Ala Ala Trp Arg Asp Glu Thr Ala Thr Phe Thr Tyr Arg
 1               5                  10                  15

Ser Arg

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ala Ser Leu Ile Trp Arg Asp Glu Thr Ala Arg Tyr Thr Lys Ser
 1               5                  10                  15

Gly Arg

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Asn Thr Lys Gln Trp Arg Asp Glu Thr Ile Lys Ala Ala Arg Leu
 1               5                  10                  15

Ile Arg

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 73

Gln Ala Leu Ala Glu Trp Arg Asp Glu Thr His Glu Ile Ser Arg Leu
 1               5                  10                  15

Ser Arg

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Gly Val Ser Lys Trp Arg Asp Glu Thr Ile Ser Leu Val Lys Tyr
 1               5                  10                  15

Val Arg

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Met Ile Gly Arg Trp Arg Asp Glu Thr Leu Pro Arg Leu Arg Ser
 1               5                  10                  15

Val Leu

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Arg Val Ile Gly Trp Arg Asp Glu Thr Gln Arg Leu Thr Ser Arg
 1               5                  10                  15

Ile Met

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Val Ile Ser Val Trp Arg Asp Glu Thr Arg Ser Ser Phe Leu Arg
 1               5                  10                  15

Thr Ser

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 78

Ala Ala Val Ser Ser Trp Arg Asp Glu Thr Lys Leu Phe Leu Thr Arg
 1               5                  10                  15

Ser Gln

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Ser Cys Gln Val Trp Arg Asp Glu Thr Arg Val Asn Thr Gln Arg
 1               5                  10                  15

Ser Ser

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Ala Met Gly Lys Trp Arg Asp Glu Thr Gln Ile Leu Ala Gln Arg
 1               5                  10                  15

Ala His

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Ser Met Asn Ala Trp Arg Asp Glu Thr Ile Lys Asn Ala Ile Ser
 1               5                  10                  15

Ser Arg

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

His Thr Ile Gly Leu Trp Arg Asp Glu Thr Leu Lys Ser Val Ala Ser
 1               5                  10                  15

Ser Arg

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Val Tyr Val Lys Glu Trp Arg Asp Glu Thr His Thr Arg Phe Val Ser
1               5                   10                  15

Thr Arg

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asn Asn Gln Arg Leu Trp Arg Asp Glu Thr Lys Thr Trp Phe Gly Met
1               5                   10                  15

Ser Arg

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Met Val His Gly Trp Arg Asp Glu Thr Val Thr Ser Ser Thr Leu
1               5                   10                  15

Thr Arg

<210> SEQ ID NO 86
<211> LENGTH: 29
<212> TYPE: PRT
<213> ORGANISM: Enterobacteria phage T7

<400> SEQUENCE: 86

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys
                20                  25

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (19)..(20)
<223> OTHER INFORMATION: Any amino acid

```
<220> FEATURE:
<221> NAME/KEY: MOD_RES
<222> LOCATION: (29)
<223> OTHER INFORMATION: Any amino acid

<400> SEQUENCE: 87

Xaa Asn Glu Ser Xaa Xaa Asn Ala Thr Asn Thr Xaa Xaa Trp Arg Asp
1               5                   10                  15

Glu Thr Xaa Xaa Phe Arg Asp Glu Ala Arg Arg Phe Xaa
            20                  25

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Asn Glu Ser Ser Thr Asn Ala Arg Ser Val Lys Thr Trp Arg Asp
1               5                   10                  15

Glu Thr Ala Arg Leu His Gln Arg Ile Leu Arg Phe Lys
            20                  25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Asn Glu Ser Ser Thr Ala Ala Thr Asn Thr Lys Gln Trp Arg Asp
1               5                   10                  15

Lys Thr Lys Gly Phe Arg Asp Glu Ala Arg Arg Phe Lys
            20                  25

<210> SEQ ID NO 90
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Asn Glu Ser Ser Thr Ala Ala Thr Asn Thr Lys Gln Trp Arg Asp
1               5                   10                  15

Lys Thr Lys Gly Phe Arg Asp Glu Ala Arg Arg Phe Lys
            20                  25

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Asn Glu Ser Ser Thr Ala Ala Thr Asn Thr Lys Gln Trp Arg Asp
1               5                   10                  15

Lys Thr Lys Gly Phe Arg Asp Glu Ala Arg Arg Phe Lys
```

```
                    20                  25

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: Any amino acid

<400> SEQUENCE: 92

Lys Asn Glu Ser Ser Thr Asn Ala Thr Asn Thr Lys Gln Trp Arg Asp
 1               5                  10                  15

Glu Thr Xaa Leu Phe Arg Asp Glu Ala Lys Arg Phe Lys
                20                  25

<210> SEQ ID NO 93
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: Any amino acid

<400> SEQUENCE: 93

Lys Asn Glu Ser Ser Thr Asn Ala Thr Asn Thr Lys Gln Trp Arg Asp
 1               5                  10                  15

Glu Thr Xaa Leu Phe Arg Asp Glu Ala Lys Arg Phe Lys
                20                  25

<210> SEQ ID NO 94
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: Any amino acid

<400> SEQUENCE: 94

Lys Asn Glu Ser Ser Thr Asn Ala Thr Asn Thr Lys Gln Trp Arg Asp
 1               5                  10                  15

Glu Thr Xaa Ser Phe Arg Asp Glu Ala Lys Arg Phe Lys
                20                  25

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Asn Glu Ser Arg Tyr Asn Ala Thr Asn Thr His Ser Trp Arg Asp
 1               5                  10                  15
```

```
Glu Thr Ile Ala Phe Arg Asp Glu Ala Arg Arg Phe Ser
            20                  25

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Asn Glu Ser Ser Ser Asn Ala Thr Asn Thr Tyr Asn Trp Arg Asp
 1               5                  10                  15

Glu Thr Arg Thr Phe Arg Asp Glu Ala Arg Arg Phe Phe
            20                  25

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Asn Glu Ser Ser Thr Asn Ala Thr Asn Thr Lys Gln Trp Arg Asp
 1               5                  10                  15

Glu Thr Lys Gly Phe Arg Asp Glu Ala Arg Arg Phe Gly
            20                  25

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Asn Glu Ser Ser Thr Asn Ala Thr Asn Thr Arg Val Trp Arg Asp
 1               5                  10                  15

Glu Thr Gln Lys Phe Arg Lys Glu Ala Leu Arg Phe Lys
            20                  25

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Asn Glu Ser Ser Thr Asn Ala Thr Asn Thr Gly Arg Trp Arg Asp
 1               5                  10                  15

Glu Thr Asp Ser Phe Arg Arg Glu Ala Arg Arg Phe Lys
            20                  25
```

T7 PHAGE PEPTIDE DISPLAY SYSTEM AND USES THEREOF

STATEMENT OF GOVERNMENT INTEREST

This invention was made with government support under DK065090 awarded by the National Institutes of Health. The government has certain rights in the invention.

FIELD OF THE INVENTION

The invention relates to a novel T7 phage display system, specifically to the use of this display system for the identification of liver-specific ligands.

BACKGROUND OF THE INVENTION

In vivo phage display has proved to be a powerful source of new peptide ligands for specific targeting of organs by drugs and gene therapy vectors (Pasqualini and Ruoslahti 1996; Trepel, Arap et al. 2002). Since the introduction of this methodology a decade ago, a number of peptides that preferentially react with organ-specific endothelium and parenchymal markers have been identified by selection experiments (Trepel, Arap et al. 2002). The liver, however, has been conspicuously missing from these studies, even though it possesses a multitude of acquired and hereditary disorders and represents one of the most important therapeutic targets (Wu, Nantz et al. 2002). Paradoxically, the liver would appear to be a particularly rewarding phage display target due to its discontinuous endothelium that provides access to liver parenchymal cells and hepatocytes by blood-borne particles as large as phage T7 (d ~60 nm) (Wisse, De Zanger et al. 1985; Sokoloff, Wong et al. 2003).

The lack of effort directed toward identification of liver-specific peptide ligands via in vivo phage display is largely accounted for by the predominant use of phage display systems based on filamentous phage M13 and fd (Pasqualini and Ruoslahti 1996). As noted in Pasqualini et al., a substantial portion of injected peptide library displayed on phage fd-tet is non-specifically sequestered by the liver, which strongly interferes with the selection of liver-specific peptides (Pasqualini and Ruoslahti 1996). A detailed study of phage clearance has shown that the commonly used display library FUSE5, containing random peptides at the N-terminus of the phage fd-tet protein pIII, disappears from the mouse bloodstream or loses its infectivity within 30 minutes after injection (Zou, Dickerson et al. 2004). The present inventors have also observed that the PhD6 library (New England Biolabs), displaying 6-mer linear peptides in pIII of phage M13, is rapidly inactivated by human serum with the apparent involvement of natural antibodies and complement. The PhD6 inactivation is inhibited by excess UV-irradiated wild-type phage, suggesting the presence in phage M13 of an invariant serum-reactive determinant (A. Sokoloff, unpublished data). A similar reactivity of filamentous phage with mouse blood constituents would explain its disappearance from the circulation and accumulation in Kupffer cells (Sokoloff, Wong et al. 2003). Also, because hepatocytes are separated from the liver sinusoids by the space of Disse, which restricts the passage of particles with a diameter >100 nm (Wisse, De Zanger et al. 1985; Molenaar, Michon et al. 2002), the use of filamentous phage for selection of peptide ligands recognized by liver parenchymal cells is hampered by the size of filamentous phage particles, which are in excess of 500 nm in length.

More recently, a phage display system utilizing the T7 bacteriophage was developed (see e.g. Novagen 1999). T7 is a double-stranded DNA phage (Dunn and Studier, 1983, J. Mol. Biol., 166:477-535), whose DNA is completely sequenced (39,937 bp) and for which a high-efficiency in vitro packaging system is available (Son et al., 1988, Virology 162:38-46). Unlike filamentous phages, phage T7 particles are icosahedral and small in size (d~60 nm; FIG. 1a), and can readily pass through the space of Disse (Sokoloff, Wong et al. 2003). The viral particle has a head which encapsulates the viral genome. The head is composed of 415 copies of the head protein or coat protein, 10B (p10B), whose C-terminus normally serves as a peptide display site (Novagen 1999). Although the T7 phage display system avoids the size-related disadvantages of the filamentous phage display system, peptides displayed on the T7 phage system are still subject to the non-specific sequestering by the liver, and as such it is unsuitable for identifying liver-specific ligands.

Due to the above limitations of filamentous phage as a peptide carrier for liver selections in vivo, and due to the non-specific sequestering by the liver of peptides displayed on prior T7 phage display systems, there is a great need for a phage-display system suitable for identification of liver-specific ligands.

Furthermore, because normal human serum contains a large population of natural IgM antibodies that collectively recognize virtually all randomly generated linear C-terminal peptides (Sokoloff, Bock et al. 2000; Sokoloff, Bock et al. 2001; Sokoloff, Puckett et al. 2004), linear C-terminal peptides as a group may be difficult to adapt as therapeutic ligands, particularly if present in multiple copies.

There is thus a further need for a phage display system that prevents the recognition of displayed sequences by natural antibodies (Sokoloff, Bock et al. 2000), the avoidance of which is of paramount importance in designing therapeutically relevant organ-specific ligands or delivery vehicles.

In addition, in prior phage display systems, the peptide is generally displayed without any structural constraint, e.g. at the N-terminal or C-terminal of the sequence to which the displayed peptide is fused. Although such unconstrained or linear peptides constitute an attractive starting point for the ligand screening or development of peptidomimetics, their use as drug lead is severely limited by e.g. the flexibility of the displayed peptides in solution, which makes it difficult if not impossible to select, from among a group of nearly iso-energetic conformations, the one biologically most relevant (Marschall, 1992, Curr. Opin. Struct. Biol. 2: 904-919). In addition, peptides generally have many unfavorable pharmacological properties, such as poor bioavailability, short duration of action, and lack of oral activity. Thus, the peptides need to be evolved into peptidomimetics for pharmaceutical applications. This in general requires the establishment of a pharmacophore model (i.e. identification of the amino acid side chains responsible for activity and determining the spatial relationship between these groups). Because only rarely can the biologically relevant peptide topology be deduced from direct observation of the receptor-ligand complex, it is very difficult to determine the spatial relationship of the responsible side chains.

It has been recognized that starting from the analysis of constrained sequences earlier in the process, i.e. during the selection phase, will help expedite the effort (Falciani et al., 2005, Chemistry & Biology 12:417-426; Becker et al., 1999, J. Biol. Chem. 274:275413-17522). A positive hit from screening a conformationally constrained peptide combinatorial library would immediately yield not only the identity of the side chain pharmacophores but also their three-dimensional arrangement as well, i.e. the information that is necessary for the design of the corresponding "scaffolded" peptidomimetic.

There is thus a further need for a method and related compositions to allow for the screening of conformationally constrained peptide libraries. The present invention satisfies these needs and provides related advantages as well.

SUMMARY OF THE INVENTION

In one embodiment, the present invention provides a bacteriophage T7 display vector for expressing and displaying an exogenous peptide, wherein the display vector comprises a polynucleotide encoding a bacteriophage T7 tail fiber protein p17 in which a hepatocyte-targeting determinant sequence is inactivated, and wherein a cloning site is contained in a coding sequence for the tail fiber protein p17 or in a coding sequence for a capsid protein p10B for insertion of an exogenous nucleotide sequence encoding the exogenous peptide. Preferably, the cloning site is in the coding sequence for p17 and the exogenous nucleotide sequence is inserted at the C terminus of p17, or in frame internally of p17. In a preferred embodiment, the vector is packaged with bacteriophage T7 capsid protein 10B which is truncated at the C-terminus at position Q343.

In one embodiment, the coding sequence encoding amino acid residue 211 of p17 is mutated to encode an amino acid other than K, or the coding sequence encoding amino acid residue 211 of p17 is mutated to encode amino acid E. Alternatively, the coding sequence encoding amino acid residue 200 or 207 of p17 is mutated to encode an amino acid other than R; preferably, the coding sequence encoding amino acid residue 200 of p17 is mutated to encode an amino acid L, or the coding sequence encoding amino acid residue 207 of p17 is mutated to encode an amino acid C.

In another embodiment, the exogenous peptide comprises at least 7 amino acid residues. Preferably, the display vector comprises a polynucleotide encoding amino acid residues 1-150 and 268-553 of p17, wherein a cloning site is contained within a coding sequence for amino acid residues 151-267 of p17 for in-frame insertion of a nucleotide sequence encoding the exogenous peptide. In one embodiment, the exogenous peptide comprises not more than 19 amino acid residues.

The display vector of the present invention preferably comprises wild-type T7 protein p17 regulatory signals, such as a promoter, or a translation initiation signal, or both. The display vector may further comprise a wild type p17 terminator.

In another embodiment, the cloning site of the display vector of the present invention is in the coding sequence for p10B and the exogenous nucleotide sequence is inserted at the C terminus of p10B, or in frame internally of p10B. Preferably, the vector is packaged with bacteriophage T7 capsid protein p10B which is truncated at the C-terminus at position Q343.

The present invention further provides a host cell containing a display vector as described above. The host cell may preferably further comprise an expression vector which comprises a nucleotide sequence coding for a wild type p17 protein operably linked to a promoter, while the display vector comprises a coding sequence for protein p17 and the exogenous peptide, operably linked to a different promoter.

The present invention further provides a bacteriophage T7 particle comprising at least one copy of a p17 protein which comprises an exogenous peptide displayed thereon, or at least one copy of a p10 protein with an exogenous peptide displayed thereon, wherein a hepatocyte-targeting determinant sequence on the bacteriophage T7 tail fiber protein p17 is inactivated.

In a preferred embodiment, the bacteriophage T7 particle according to the present invention comprises at least one copy of a p17 protein which comprises an exogenous peptide displayed thereon; preferably, the bacteriophage T7 particle further comprises a wild type copy of p17 protein in addition to the at least one copy of a p17 protein which comprises an exogenous peptide displayed thereon.

In another preferred embodiment, the bacteriophage T7 particle comprises at least one copy of a p10 protein with an exogenous peptide displayed thereon; preferably, the bacteriophage T7 comprises a wild type copy of p17 protein. Preferably, the bacteriophage T7 particle comprises a p10 protein which is truncated at position Q343.

The present invention further provides a viral lysate containing assembled bacteriophage T7 particle described above.

The present invention in another embodiment provides a method for determining if a candidate peptide is a liver-targeting peptide, the method comprising 1) providing a bacteriophage T7 display vector as described above, wherein a nucleotide sequence encoding the candidate peptide is inserted at the cloning site for in-frame expression thereof; 2) packaging the bacteriophage T7 display vector into a replicating bacteriophage T7 displaying the candidate peptide and optionally amplifying the packaged bacteriophage T7 displaying the candidate peptide; 3) administering the packaged bacteriophage T7 displaying the candidate peptide into a mammal; and 4) determining whether the packaged bacteriophage T7 displaying the candidate peptide distributes to the liver of the mammal, wherein preferential distribution of packaged bacteriophage T7 in the liver indicates that the candidate peptide is a liver-targeting peptide.

Preferably, the above method is used for screening for liver targeting peptides. Specifically, the method of the invention for liver targeting ligand screening comprises: 1) providing a library of nucleic acid sequences encoding a library of candidate peptides; 2) preparing a library of packaged T7 bacteriophages displaying the library of candidate peptides, 3) administering the library of packaged T7 bacteriophages displaying the candidate peptides to a mammal; and 4) selecting for packaged T7 bacteriophages that accumulate preferentially in the liver of the mammal, wherein the one or more candidate peptides displayed in the packaged T7 bacteriophages accumulated in the liver are liver-targeting peptides. In a preferred embodiment, the above method further comprise 5) amplifying the selected T7 bacteriophages from step 4), 6) administering the amplified T7 bacteriophages to a second mammal, and 7) selecting for T7 bacteriophages that accumulate preferentially in the liver of the second mammal, wherein the one or more candidate peptides displayed in the packaged T7 bacteriophages accumulated in the liver of the second mammal are liver-targeting peptides with higher specificity. Preferably, the above steps 5)-7) are repeated at least once.

BRIEF DESCRIPTION OF THE DRAWINGS

FIG. 1(a) is a schematic depiction of Phage T7. The tail fiber site containing a hepatocyte-targeting determinant is circled; FIG. 1(b) is a cross-sectional view of the p17 coiled-coil domain containing the hepatocyte-targeting determinant. The hydrophobic interactions between residues in positions a and d and electrostatic interactions between residues in positions e and g are shown as dashed lines; FIG. 1(c) is the p17 domain structure; (d) shows phage vector design; and (e) depicts incidence of various residues at randomized p17 positions for the 7-mer library.

Figure 2:
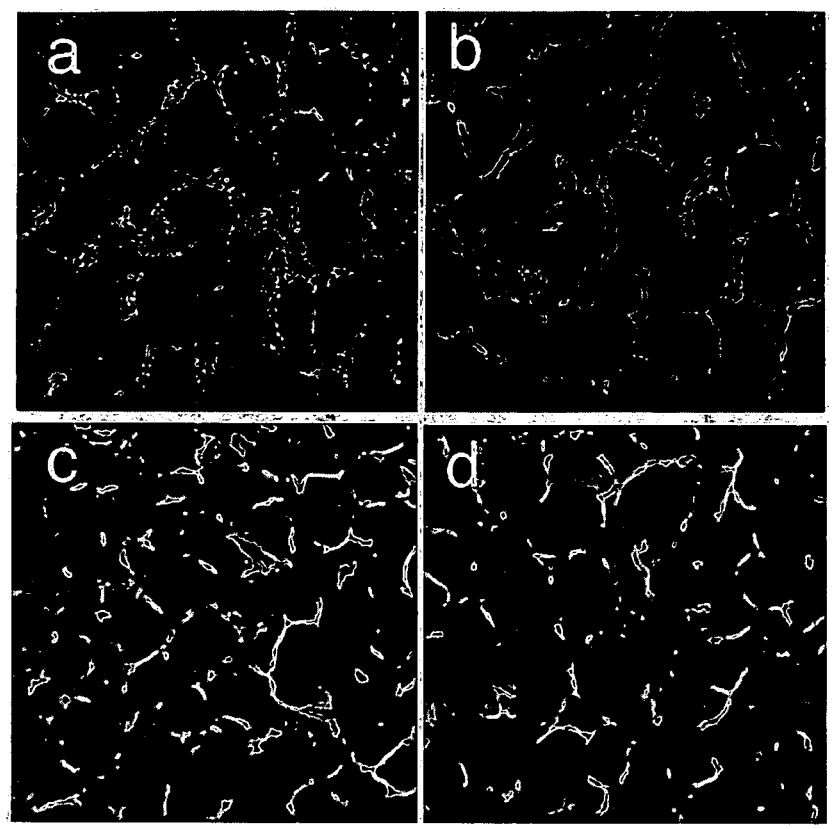

FIG. 2 shows the immunohistochemical liver targeting by p17-displayed sequences derived from ApoB (a) and ApoE (b). Phage 20-6 (c), which does not target liver (Sokoloff, Wong et al. 2003), and PBS (d) were used as negative controls. Green, blue, and red colors correspond to F-actin, nuclear, and phage staining, respectively.

Figure 3:
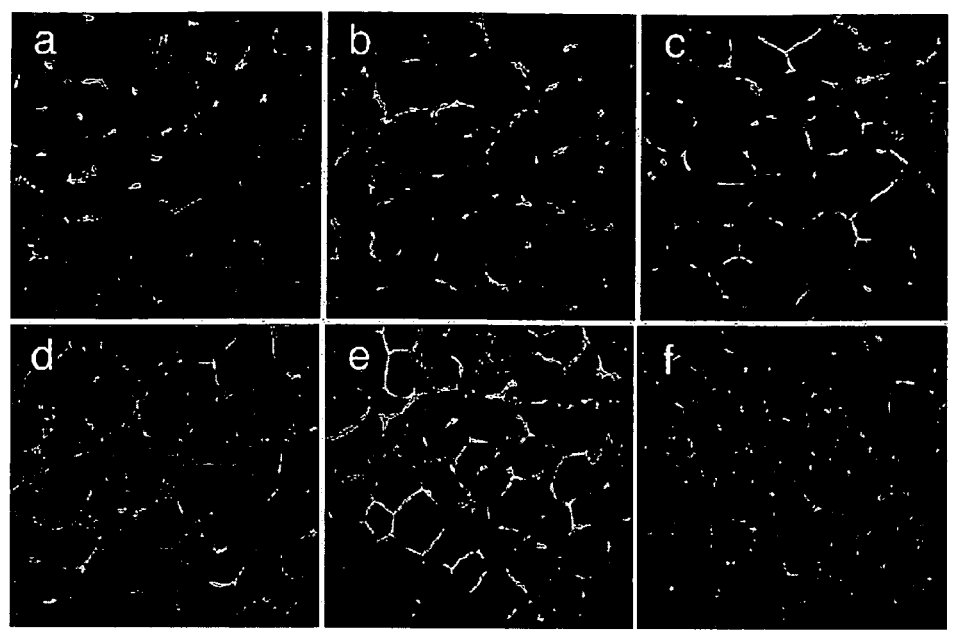

FIG. 3 shows immunohistochemical localization of phage clones selected from the 7-mer library. (a-c) Hepatocyte-targeting clones 1-10, 1-18, and 2-38, respectively (Table 2, "#"). (d-f) Sinusoid-targeting clones 1-5, 1-19, and 1-21, respectively (Table 2, "#"). Green, blue, and red colors correspond to F-actin, nuclear, and phage staining, respectively.

Figure 4:
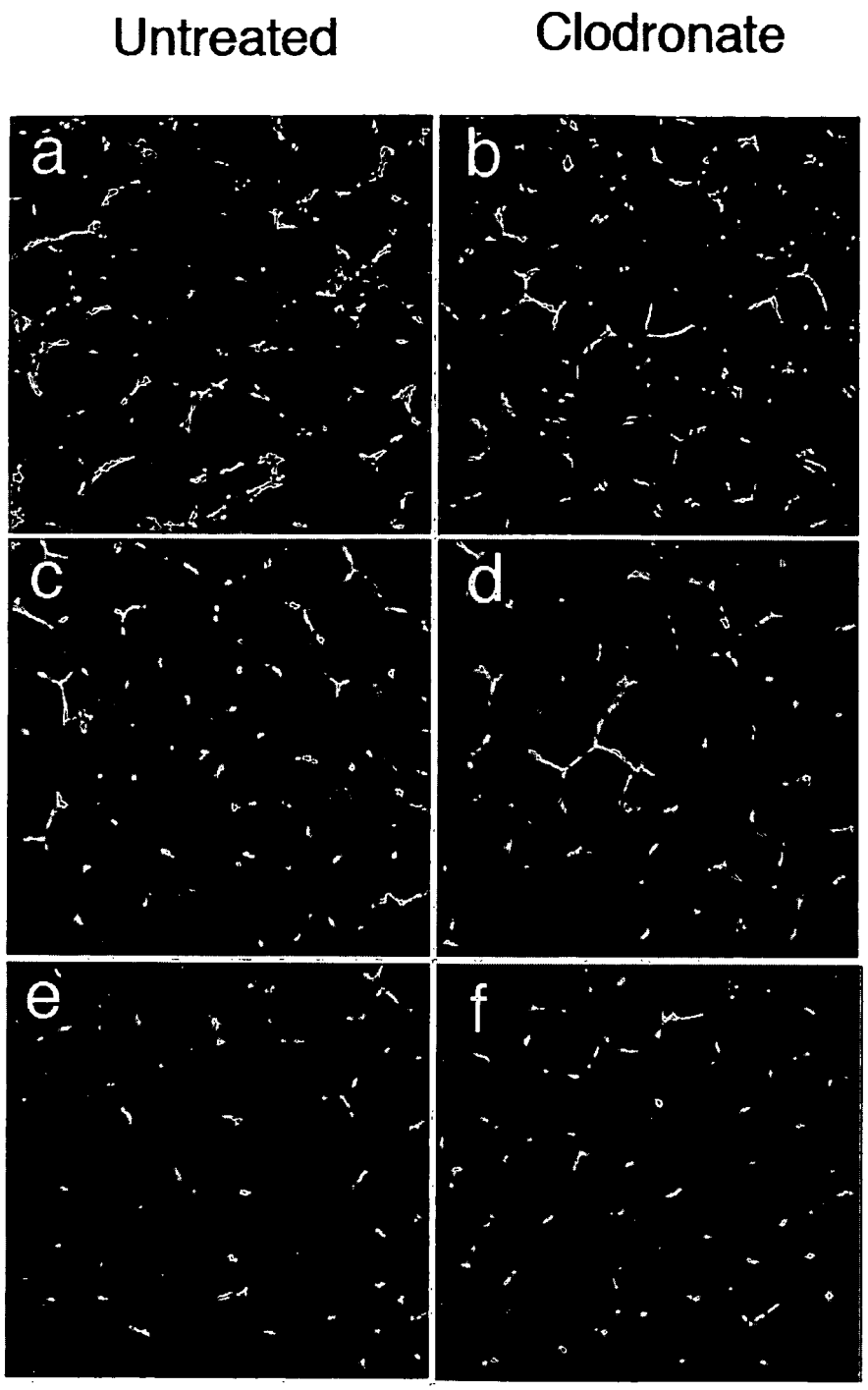

FIG. 4 shows immunohistochemical localization of phage clones selected from the 7-mer library in clodronate pre-injected ICR mice. (a, b) Clone 20-6F. (c, d) Clone IL-1m. (e, f) Clone 1-21. Green, blue, and red colors correspond to F-actin, nuclear, and phage staining, respectively.

Figure 5:
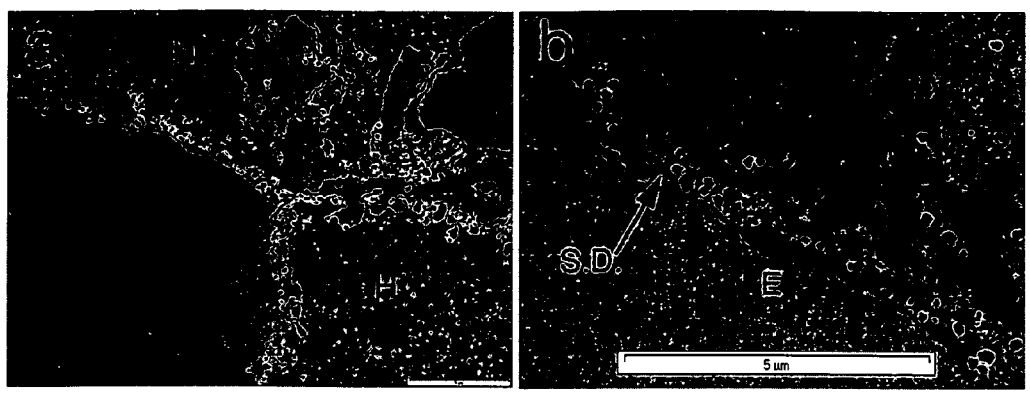

FIG. 5 is a typical electron microscopy image of a sinusoid region containing sinusoid-targeting phage 1-21. (a) Sinusoid regions of two adjacent hepatocytes. (b) A close-up of the sinusoid region shown in the image on the left. H—hepatocyte, E—endothelial cell, S.D.—space of Disse. Scale bars—5 µm.

FIG. 6A shows the partial amino acid sequence of p10b protein (SEQ ID NO: 10) and the truncated sequence in Clone 20-6 (SEQ ID NO: 11). FIG. 6B shows the comparison of the partial nucleotide sequence of the hepatocyte-targeting determinant region of the p17 protein. The top sequence is that of Clone 20-6 (SEQ ID NO: 12), which differs from the wild type only at the position 211 (on point mutation from A to G; grey highlighted and underlined yellow highlight) which encodes K in the wild type phage but for E in Clone 20-6. The bottom sequence is the modified sequence (SEQ ID NO: 13), on which other Other changes to introduce cloning sites are highlighted in grey blue. The first T>G change introduces the BspEI site. The CAACG>GAATTC introduces the EcoRI site. The AA>CT introduces the HindIII site, and the T>G introduces the SacII site.

DETAILED DESCRIPTION OF THE INVENTION

The novel T7 phage display system of the present invention provides a powerful approach to analyzing peptide sequences for liver targeting in vivo and to discovering new liver-targeting peptide sequences, as well as to screening conformationally constrained peptide libraries for the identification of ligands with high binding affinity and for the establishment of pharmacophores useful in rational drug designs. In preferred embodiments, the present phage display system may be used for the identification of high-affinity liver targeting ligands.

In one embodiment, the novel display system of the present invention is a "stealth" in vivo phage display system, and polypeptides displayed on the system of the present invention are not sequestered by the liver, or are unrecognizable by the innate immune system of the host, or both. Accordingly, the novel phage display system is well suited for selection of novel liver-specific ligands.

Stealth Phage Display for Screening Liver Targeting Peptides

As discussed above, the viral coat of the T7 phage is composed of 415 copies of the head protein, 10B (p10B), whose C-terminus normally may serve as a peptide display site (Novagen 1999). It is known that truncation of p10B at the C-terminal after its residue $Q_{343}$ abolishes the recognition of the phage by natural IgM antibodies that specifically react with protein C-terminal sequence. This truncation also prevents phage uptake by Kupffer cells that apparently recognize phage through complement protein fragments attached to the phage surface as a result of complement activation by IgM-phage complexes (Sokoloff, Bock et al. 2000; Sokoloff, Wong et al. 2003; Sokoloff, Puckett et al. 2004).

Figure 1:
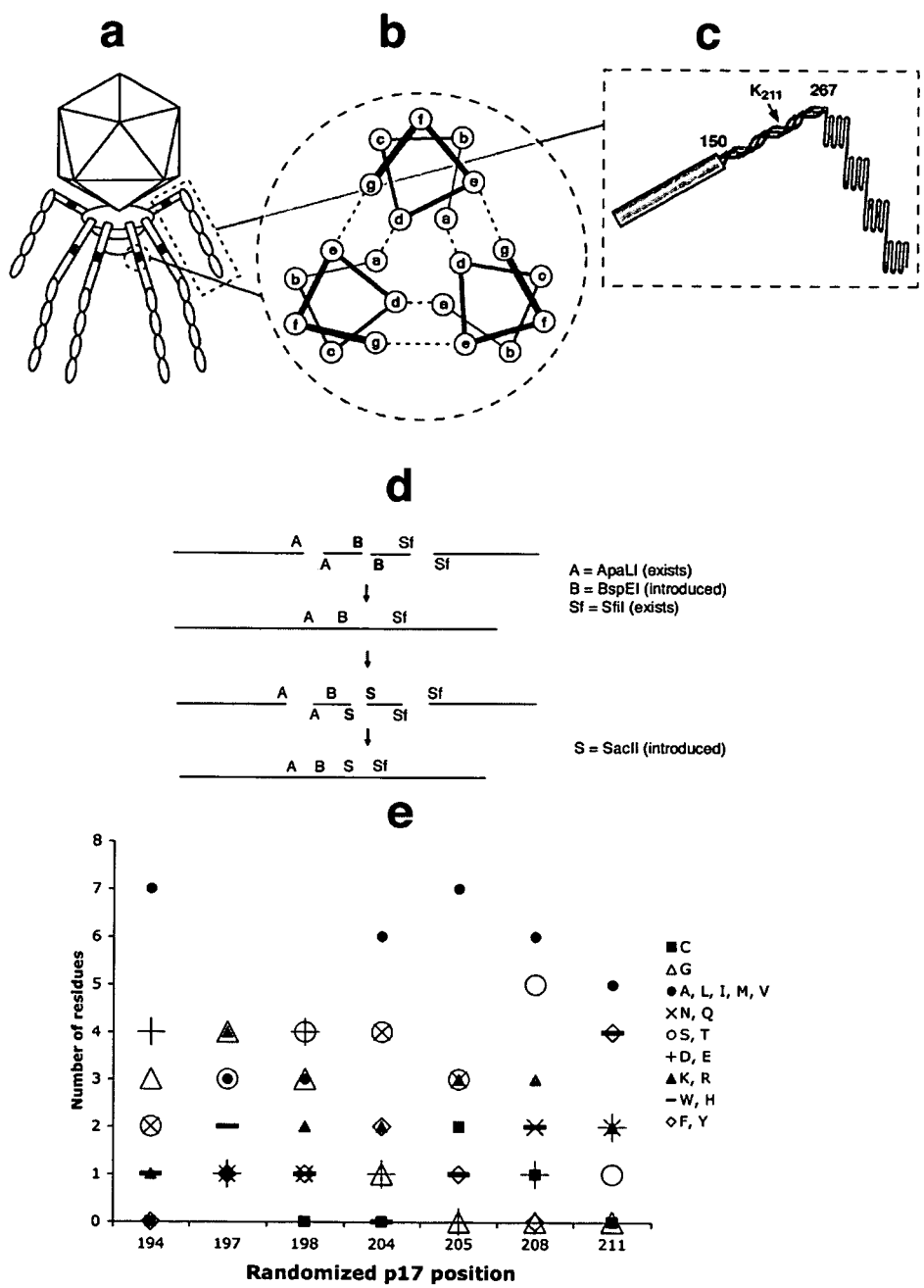

The T7 phage further has a small tail composed of six tail fibers (FIG. 1, a). Each fiber is composed of three copies of protein p17 and consists of an N-terminal domain (residues 1-150) followed by a coiled-coil rod-like domain (residues 151-267; FIG. 1b) and a C-terminal half of the protein (residues 268-553) that includes four domains (FIG. 1c; Steven, Trus et al. 1988).

The p17 protein comprises a specific hepatocyte-targeting determinant region (FIG. 1a, circled). This region is located within the coiled-coil rod-like domain (residues 151-267), within two adjacent heptads of the coiled-coil domain. Three point mutations located within this region are known to disrupt phage uptake by hepatocytes. The first is a single point mutation ($K_{211} \rightarrow E$) (Sokoloff, Wong et al. 2003), and the other two are $R_{207} \rightarrow L$ and $R_{200} \rightarrow C$ (Sokoloff, Wong et al. 2003). The presence of a compact hepatocyte-targeting determinant in this region has been further confirmed by producing fusion proteins and synthetic peptide conjugates that specifically target hepatocytes (Sokoloff, Wong et al. 2003; Wong, Wakefield et al. 2006).

In one embodiment, a stealth phage display system of the present invention is designed by eliminating or disrupting the hepatocyte-targeting function of this region, preferably by introducing one or more of the above three point mutations. A phage particle without the hepatocyte-targeting function will not be nonspecifically sequestered by the liver, and accumulation into the liver of phage particles displaying a peptide indicates that the displayed peptide has liver targeting activities.

Candidate peptides may be displayed on any suitable display site of the phage particle. The peptide for example may be displayed on the p17 tail protein, or on the head protein p10B.

When peptide sequences are displayed at the p17 site, they are readily accessible to cell surface receptors.

Peptides to be displayed on the stealth phage display system of the present invention may also be on the coat protein. One advantage of displaying the candidate or exogenous peptides on the coat protein is that it allows for display of a very high copy number of the candidate peptides.

The use of 10B capsid protein for displaying exogenous peptides is well within the skills of the art. Depending on the size of the exogenous peptides to be displayed, two types of display vectors can be selected, one for high-copy number display of peptides, and one for low copy number display of larger peptides. In either case, coding sequences for the peptides to be displayed are cloned within a multiple cloning site, typically following aa 348 of the 10B protein. The natural translational frameshift site within the capsid gene may preferably be removed, so only a single form of capsid protein is made from these vectors.

For high copy number display, expression of the capsid gene with the coding sequence for the exogenous peptide is preferably controlled by the same strong phage promoter (e.g. φ10) and translation initiation site (e.g. s10) as in wild-type phage, and the capsid/peptide fusion protein is produced in large amounts during infection. A suitable host strain, e.g. E. coli strain BL21, may be used as host for these clones, and the capsid shell of the phage is composed entirely of the capsid/peptide fusion protein, thereby displaying 415 copies of peptide on the surface of the phage. High copy number display is desirable wherever a strong signal is useful, such as in epitope mapping. It may also be important for obtaining peptides that at best bind only very weakly to their targets.

Longer peptide sequences (e.g. up to about 1000 amino acids) may also be displayed using a low copy number (about 0.1-1 per phage) vector system.

In order to obtain low-copy display, the wild-type promoter of the capsid gene is removed and the translation initiation site altered. The capsid mRNA is still produced from phage promoters located further upstream of the gene, but production of capsid protein is greatly reduced. A complementing host (e.g. BLT5403) is used that provides large amounts of the 10A capsid protein from a plasmid clone. Unlike the high-copy number vector system, in which the copy number of displayed peptides is fixed by the number of capsid proteins in the T7 capsid shell (415), the display number from the low-copy number vector system is not similarly fixed. It presumably depends on the ratio of expression of the capsid fusion protein from the vector and the 10A protein from the complementing host (BLT5403 or BLT5615), and also on the efficiency of assembly of the fusion protein into the capsid shell.

The 10A gene in the complementing plasmid and the capsid gene in the vectors are engineered to minimize any recombination between the genes, using methods well-known in the art. Low copy number display systems are suitable for the selection of proteins that bind strongly to their targets.

The phage display system of the present invention further optionally abolishes the recognition of the phage by natural IgM antibodies, which also prevents phage uptake by Kupffer cells, preferably by packaging the displaying vector with a phage p10B protein with the truncation at $Q_{343}$.

Display at p17 Site with Constrained Configuration

In a preferred embodiment, candidate peptides are displayed in the system of the present invention in a constrained configuration. Specifically, the peptides are displayed internally on the tail fiber of phage T7.

As indicated above, such internal, conformationally constrained display typically allows selection of ligands with a binding affinity higher than that of peptides displayed in non-constrained or linear configuration, and promotes selection of stable and efficacious ligands (Falciani, Lozzi et al. 2005). Ligands thus selected also more easily avoid recognition by natural antibodies (Sokoloff, Bock et al. 2000).

Any internal sites of p17 can serve as a display site. The present inventors have surprisingly discovered that the p17 is capable of harboring a large variety of random sequences without significant reduction in phage viability. While not willing to be bound by any current understanding of the underlying mechanism, the present inventors believe that this ability of the p17 display site to accommodate a wide variety of sequences is due to the alignment shift of the individual tail fibers. Specifically, an individual tail fiber is composed of three p17 chains that are oriented in the same direction but apparently shifted relative to each other by one, or more likely, a few heptads (FIG. 1, b and c; (Steven, Trus et al. 1988)). Therefore, while the substitution of the wild-type p17 sequence by a random sequence in a domain composed of perfectly aligned p17 chains would probably "break" its rod-like configuration and significantly reduce phage viability; the alignment shift is likely to mitigate the impact of such substitution. The above is especially true with regard to the coiled-coil display region.

Methodology similar to using p10B capsid protein for displaying exogenous peptides is used to display exogenous peptides on the T7 tail fiber protein. Depending on the size of the exogenous peptides to be displayed, two types of display vectors can be selected, one for display of peptides of shorter sequence which does not significantly disrupt the function of the tail fiber/exogenous peptide fusion protein, and one for low copy number display of larger peptides. In either case, coding sequences for the peptides to be displayed are cloned within a multiple cloning site engineered onto the tail fiber protein coding sequence.

For shorter sequence display, expression of the tail fiber protein with the coding sequence for the exogenous peptide is preferably controlled by the same phage promoter and translation initiation site as in wild-type phage, and 100% of the copies of the protein expressed are the tail fiber/exogenous peptide fusion protein during infection in a suitable host strain. The tail fiber of the phage is composed entirely of the fusion protein, thereby displaying 18 copies of the exogenous peptide on the tail fiber the phage.

For displaying longer peptide sequences (e.g. up to about 1000 amino acids) on the tail fiber, the wild-type promoter of the tail fiber gene is modified to reduce expression. The level of expression of the tail-fiber/exogenous fusion protein is controlled by manipulating the strength of the promoter controlling the fusion protein production.

A plasmid that expresses the wild-type tail fiber protein is constructed, using methods well-known to those skilled in the art. A suitable host strain is transformed with this plasmid, and serves as the complementary host for the phage construct containing the tail-fiber/exogenous peptide fusion protein. The plasmid is maintained in the bacterial, e.g. using an antibiotic. The plasmid may comprise an inducible promoter (such as an IPTG inducible promoter) in case the p17 protein is toxic at high levels by itself to the host, or a constitutive promoter. Alternatively, the entire expression cassette from the T7 phage can be cloned and put into a bacteria. If necessary, the expression of the tail fiber protein can be attenuated by changing various bases of the promoter.

When this complementary host is infected with the phage construct containing the tail-fiber/exogenous peptide fusion protein, both the fusion protein and wild-type tail fiber will contribute to the final tail fiber product and packaged onto the phage particles. The contribution from the plasmid, and consequently, the phage, would be regulated by having different promoter strengths for the plasmid and phage. Specifically, a strong plasmid promoter/weak phage promoter combination will result in low contribution from the phage and a low copy number of the displayed peptide; a strong plasmid promoter coupled with a strong phage promoter will result in nearly equal contribution from phage and plasmid, and a weak plasmid promoter/strong phage promoter will result in relatively high copy number of the displayed peptide. An ordinarily skilled person in the art would be able to manipulate the copy number by recognizing the need to maintain phage viability or infectivity, and the need to have adequate number of displayed peptides for screening and identification purposes, and achieve a suitable balance thereof. For example, the wild type promoter which regulates p17 expression in phage T17 should preferably be maintained for controlling the fusion protein expression, while the strength of the promoter driving the expression of the plasmid-derived tail fiber is manipulated.

The ratio of tail fiber contributed by plasmid versus phage genome can be determined using SDS/PAGE, and, if necessary, western blots.

It is preferable that the plasmid derived tail fiber is engineered to contain the non-liver targeting sequence. More preferably, both the phage derived and plasmid-derived tail-fiber proteins are non-liver targeting.

The phage display system of the present invention further may or may not abolish the recognition of the phage by natural IgM antibodies, which also prevents phage uptake by Kupffer cells. In other words, packaging of the displaying vector may be with a phage p10B protein with or without the truncation at $Q_{343}$.

Screening for Liver Targeting Peptides with Constrained Conformation

The constrained conformation display may further be combined with the stealth feature of the present display system. In other words, if there is a need to target liver, the candidate peptides would be displayed internally on p17, and the liver targeting functions of the p17 protein are also eliminated. Preferably, the stealth phage display system of the present invention utilizes the p17 coiled-coil rod-like domain (residues 151-267) as the display site.

The present inventors have surprisingly discovered that the p17 is capable of harboring a large variety of random sequences in such constrained configuration without significant reduction in phage viability. While not willing to be bound by any current understanding of the underlying mechanism, the present inventors believe that this ability of the p17 display site to accommodate a wide variety of sequences is due to the alignment shift of the individual tail fibers. Specifically, an individual tail fiber is composed of three p17 chains that are oriented in the same direction but apparently shifted relative to each other by one, or more likely, a few heptads (FIG. 1, b and c; (Steven, Trus et al. 1988)). Therefore, while the substitution of the wild-type p17 sequence by a random sequence in a domain composed of perfectly aligned p17 chains would probably "break" its rod-like configuration and significantly reduce phage viability; the alignment shift is likely to mitigate the impact of such substitution. The above is especially true with regard to the coiled-coil display region.

Similarly, the phage display system of the present invention further may or may not abolish the recognition of the phage by natural IgM antibodies, which also prevents phage uptake by Kupffer cells. In other words, packaging of the displaying vector may be with a phage p10B protein with or without the truncation at $Q_{343}$.

The materials and methods for constructing phage expression vectors, including the engineering of a cloning site, synthesis of and inserting DNA sequences to be expressed, choices and availability of promoters and other transcription regulatory sequences, choice and availability of bacterial (in particular *E. coli*) host strains with necessary genetic modifications or suitable genetic background (e.g. suppressing, in vitro packaging, plaque assay, phage lysate preparation, storage and amplification) are well established and known to those ordinarily skilled in the art. Screening phage display libraries (e.g. by biopanning); PCR amplification of selected plaques; sequence analysis of selected candidate sequences, and further rounds of screening when necessary or desired, are also well known to those skilled in the art, and is described in the literature, such as in the Novagen T7Select® System Manual (2002, Rev. B0203), and in Sambrook et al., Molecular Cloning: A Laboratory Manual, (Cold Spring Harbor Laboratory Press, 2000), both of which are hereby incorporated by reference.

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Phage Display of Peptides and Proteins (Kay et al., 1996); Phage Display, A Laboratory Manual (Barbas et al., 2001) Current Protocols in Molecular Biology (Ausubel et al., eds., (2007).

EXAMPLES

Materials and Methods

P17 Library Construction

PCR-generated DNA fragments and restriction sites used for the construction of the p17 display site are schematically shown in FIG. 1d and were prepared as follows. A PCR fragment termed "BspEI fragment 1" that encompassed the unique ApaLI site (position 31,490) and a new BspEI site (position 32,513) was generated using genomic DNA isolated from mutant phage 20-6 ($K_{211} \rightarrow E$; (Sokoloff, Wong et al. 2003)) and primers

```
                                         (SEQ ID NO: 1)
5' GAGTACTTGGAGCGTGCACTGGACCCAAC 3'
and
                                         (SEQ ID NO: 2)
5' AAGTCTCAGCCTCATTcCGGAACTGTAAGG 3'.
```

A fragment termed "BspEI fragment 2" was generated in a similar manner using the new BspEI site (position 32,513) and a preexisting unique site recognized by SfiI (position 33,309) with primers

```
5' CCTTACAGTTCCGgAATGAGGCTGAGACTT 3' (SEQ ID NO: 3)
and
5' CCATCAGTGGCCACAACGGCCTGACCTAC 3'. (SEQ ID NO: 4)
```

Phage 20-6 genomic DNA was digested with ApaLI and SfiI and then dephosphorylated and ligated in a 4-way fashion with "BspEI fragment 1" digested with ApaLI and BspEI and "BspEI fragment 2" digested with SfiI and BspEI. The ligated and amplified DNA was used with primers

```
                                         (SEQ ID NO: 5)
5' GAGTACTTGGAGCGTGCACTGGACCCAAC 3'
and
                                        ((SEQ ID NO: 6)
5' CGTTTACCTCAGATTGATGCGCcGCGGAAGCA 3'
``` to generate a fragment termed "SacII fragment 1" that included the unique ApaLI site (position 31,490), a new site recognized by SacII (position 32,687), and the BspEI site introduced in the previous step. A fragment termed "SacII fragment 2", containing a new SacII site (position 32,687) and the unique SfiI site (position 33,309), was produced in similar manner using primers

```
                                         (SEQ ID NO: 7)
5' TGCTTCCGCgGCGCATCAATCTGAGGTAAACG 3'
and
                                         (SEQ ID NO: 8)
5' CCATCAGTGGCCACAACGGCCTGACCTAC 3'.
```

The clone containing the new BspEI site only was digested with ApaLI and SfiI and then dephosphorylated and ligated in a 4-way fashion with "SacII fragment 1" digested with ApaLI and SacII and "SacII fragment 2" digested with SfiI and SacII. The ligated DNA was packaged and the resultant phage was amplified in *E. coli* BL21 cells (Novagen 1999). The DNA isolated from the amplified phage was digested with BspEI and SacII and then dephosphorylated and ligated at a ratio of 3:1 with a DNA fragment encoding random peptides. The latter was prepared by annealing two oligonucleotides that contained a 12-base overlap at 3' ends and biotin residues at 5' ends and encompassed together the entire region between the BspEI and SacII sites. The annealed oligonucleotides were filled with Klenow polymerase and digested with BspEI and SacII. The digest was incubated with streptavidin and run on a 2% agarose gel. DNA of the proper size (~174 bp) was purified using a Qiagen Qiaex II kit.

Phage Packaging and Growth

Low-background packaging extract was prepared using two quadruple T7 mutants, $T7_{4,9,10,17}$ and $T7_{5,19,10,17}$. The E. coli suppressor strain 0-11' and two original double T7 mutants that contained suppressor mutations in genes 4 and 9 and genes 5 and 19 and were thus unable to propagate in wild type E. coli were a generous gift of Dr. Phil Serwer of Department of Biochemistry at the University of Texas Health Science Center at San Antonio, 7703 Floyd Curl Drive, San Antonio, Tex. 78229-3900. Gene 10 was mutated to generate a p10B truncated after Q343 and gene 17 was mutated by substituting $K_{211}$ with an E as described in Sokoloff, Wong et al. 2003.

The packaging extract was made according to Son et al (Son, Hayes et al. 1988; Son, Hayes et al. 1989). Library DNA was packaged, amplified, and titered according to the Novagen protocol (Novagen 1999). Libraries containing $1-5 \times 10^7$ different clones were typically produced. Phage clones displaying apolipoprotein B (ApoB) and apolipoprotein E (ApoE) sequences were grown at 25° C. since their assembly was impaired at 37° C.

ApoE and ApoB constructs The ApoE sequence HLRKL-RKRLLR DADDLQKR(SEQ ID NO: 9) (residues 140-158), mediating ApoE binding to hepatic heparan sulfate proteoglycans (HSPG) in the absence of lipoproteins (Weisgraber, Rall et al. 1986; Shimano, Namba et al. 1994), and ApoB sequence LSVKAQYKKNKHRHSI (SEQ ID NO: 14) (residues 3144-3159; (Weisgraber and Rall 1987)), implicated as a part of the ApoB determinant reacting with HSPG and LDL receptor (Olsson, Camejo et al. 1997), were substituted for the p17 display region residues 206-224 and 204-219, respectively, as described above.

Animal Studies

Male Rag-1 mice and ICR mice (18-22 g) from our colony and Charles River Lab, respectively, were used. All animal studies were done according to the protocols approved by the Institutional Animal Care and Use Committee.

Selections

Phage library ($5 \times 10^{10}$ pfu) was injected into mice through the tail vein and, 30 min later, mice were injected with 20 U of heparin and livers were removed and perfused with 20-30 ml of PBS and homogenized in PBS containing 1M NaCl and 2% Triton X-100. A small portion of homogenate was saved for phage titering and the remainder was used to infect a 500 ml culture of E. coli BL21. Amplified and purified phage was used as input phage in the next selection round (Novagen 1999).

Immunohistochemistry

Phage ($10^{11}$ pfu) was injected into mice through the tail vein. Mice were killed 30 min later and phage was detected in the liver by confocal microscopy as described previously (Sokoloff, Wong et al. 2003).

Electron Microscopy $4.4 \times 10^{12}$ pfu of clone 1-21 was injected through the tail vein. After 30 min, the liver was perfused with PBS/Heparin, then with 4% formaldehyde/0.1% gluteraldehyde in 0.1M phosphate buffer. Perfused liver samples, trimmed into 3 mm cubes and further cut into 100 μm sections, were fixed for 30 min in 4% paraformaldehyde/0.1% glutaraldehyde in 0.1M phosphate buffer (PB) at room temperature and then rinsed and treated for 10 min with freshly prepared 0.1% sodium borohydride in 0.1 M PB to quench aldehydes. Next, sections were permeabilized for 30 min with 0.1% Triton X-100 in PBS, rinsed 3×10 min with PBS, and blocked with 5% BSA, 0.1% cold water fish gelatin, and 5% normal goat serum in PBS (Aurion Immuno Gold Reagents) for 30 min. Sections were then rinsed 3×10 min with incubation buffer (IB), containing PBS and 0.1% BSA-C (Aurion Immuno Gold Reagents), and incubated overnight with anti-T7 antibody in IB at 4° C. Next day, sections were rinsed 12×10 min with IB and then incubated overnight with Ultra Small gold conjugate (F(ab')$_2$ fragment of goat-anti-rabbit IgG (H&L), Aurion Immuno Gold Reagents), at 1:100 dilution, at 4° C. The incubation was stopped by washing sections 6×10 min with IB followed by washing 6×5 min with PBS. Sections were post-fixed for 30 min in 2% glutaraldehyde and washed 2×5 min with 0.1 M PB followed by washing 3×10 min with Enhancing Conditioning Buffer followed by developing in Silver Enhancement Solution (Aurion Immuno Gold Reagents) for 1.25 hours. The enhancement reaction was stopped by transferring sections into to 0.3 M sodium thiosulfate in ECS for 5 min. Next, sections were rinsed 2×10 min with ECS and then fixed in 0.5% osmium tetroxide in 0.1M PB for 30 min. Post-fixed sections were dehydrated in a graded ethanol series followed by propylene oxide and flat-embedded in Spurr's epoxy resin. Embedded samples were sectioned using a Reichert-Jung Ultracut-E Ultramicrotome and contrasted with Reynolds lead citrate and 8% uranyl acetate in 50% EtOH. Ultrathin sections were analyzed with a Philips CM120 electron microscope and images were captured with a MegaView III side mounted digital camera.

Statistics

The difference between experimental values was considered statistically significant when a p value determined for a two-tailed distribution was <0.05.

Example 1

Preparation of Phage T7 with a p17 Display Site

Our initial attempts to prepare a phage vector with a p17 display site were hampered by the recombination between modified phage DNA and the wild-type DNA present in the Novagen packaging extract. The ultrasonication of the extract for 10 min reduced the level of recombination by ~200 fold, allowing the introduction into gene 17 of unique cloning sites. The residual recombination that might produce significant background in liver selections was eliminated by using the "in-house" extract prepared from the "packaging" phage modified by truncating p10 after its Q343 (VVFQ*) (SEQ ID NO: 15) (see FIG. 6A, which shows the wild type p10b partial sequence (SEQ ID NO: 10), and the p10b sequence found in clone 20-6 (SEQ ID NO: 11), which prevents the recognition of phage by natural IgM (Sokoloff, Bock et al. 2001), and mutating p17 ($K_{211}$→E), which disrupts the phage liver targeting (Sokoloff, Wong et al. 2003). With these modifications, any recombination between vector DNA and DNA from the packaging extract would produce long-circulating phage incapable of contributing to selection output (Sokoloff, Wong et al. 2003).

The region of the p17 hepatocyte-targeting determinant region as modified to include a cloning site and to remove the hepatocyte-targeting activity is shown in FIG. 6B (SEQ ID NOs: 12 and 13). The top sequence is 20-6 sequence, which differs from the wild type by only one substitution of G for the A in the wild type sequence. This effectively changes the codon from encoding K211 to encoding an E residue. The first T>G change introduces the BspEI site. The CAACG>GAATTC introduces the EcoRI site. The AA>CT introduces the HindIII site, and the T>G introduces the SacII site. The BspEI and SacII introductions do not alter amino acids. The EcoRI and HindIII sites introduced do cause missense mutations.

Example 2

Displaying Peptide Libraries in p17

Three different libraries were displayed in p17. In two libraries, with seven and eight random residues (7-mer and 8-mer library, respectively), only the exposed positions of the p17 three-stranded coiled-coil were randomized (FIG. 1c, positions b, c, and f). The general structure of displayed peptides is shown in the top rows of Table 2 and Table 4. The general structure of codons encoding variable residues in the 7-mer and 8-mer libraries was NNN and NNY, respectively. Consequently, the 8-mer library was devoid of stop codons, as well as K, W, E, M and Q residues.

The third library, a 13-mer, contained clusters of five and eight adjacent random residues encoded by codons with the general structure NNN in p17 positions 194-198 and 204-211 (Table 3, top rows). Residues 199-202 were invariant in all three libraries as they corresponded to the annealing region of library-encoding oligonucleotides. The usage of different residues at randomized positions was studied by sequencing twenty clones from the 7-mer library. With the exception of proline, which was not present at all, residues with positively and negatively charged, aliphatic, and aromatic side chains were detected in the majority of randomized positions (FIG. 1e). Qualitatively, this indicated that the p17 coiled-coil display region could harbor a large variety of random sequences without significant reduction in phage viability.

The Display Site is highly exposed and sequences at least 19 residues long can be displayed in p17 without abrogating phage infectivity The p17 display system is tested using a known liver-targeting peptide sequence derived from Apo E. The strong hepatocyte targeting exhibited by the wild type p17 (Sokoloff, Wong et al. 2003) suggested that displayed sequences, replacing the hepatocyte-reactive determinant, would also be highly exposed and, therefore, accessible to cell surface and extracellular matrix components. The accessibility of an unrelated displayed sequence was qualitatively tested by displaying in p17 an internal ApoE sequence (residues 3144-3159; (Weisgraber, Rall et al. 1986)) that mediates ApoE binding to hepatic subendothelial HSPG (Shimano, Namba et al. 1994). It was expected that, if displayed in a functionally meaningful manner, this sequence would target phage to the space of Disse. Indeed, a substantial portion of "Apo E" phage injected into mice accumulated in liver sinusoid regions as shown by immunohistochemistry (FIG. 2b). Clone 20-6, which does not target liver (Sokoloff, Wong et al. 2003), was used as a negative control and found to be largely absent from the sinusoids when injected under identical conditions (FIG. 2c). Small amounts of 20-6 phage observed in sinusoidal regions were evidently due to the use of unperfused livers, which was required to avoid perfusion-related changes in liver morphology. The "ApoE" liver targeting suggested that (i) the accessibility to macromolecules of the p17 region containing the peptide display site is a general characteristic of the p17 coiled-coil domain, (ii) at least some continuous targeting sequences displayed in p17 maintain their functional conformations, and (iii) sequences at least 19 residues long can be displayed in p17 without abrogating phage infectivity.

Selection of liver targeting peptides The injection of p17 peptide libraries into ICR mice, which have an intact immune system, showed that 0.75-3.5% of the input phage was associated with liver in 30 min after injection (Table 1, round 1). The relatively high phage uptake observed for the 7-mer phage in the first two rounds of selection was apparently caused by incomplete liver perfusion. However, given that up to 90% of phage with the wild-type p17 is taken up by liver under these conditions (Sokoloff, Wong et al. 2003), the observed initial phage uptake was still at an acceptable level. Indeed, ~75% of the 7-mer phage was sequestered by the liver in the $6^{th}$ round of selection, which suggested a significant enrichment for liver-specific clones (Table 1, round 7). At least for selections with 13-mer and 8-mer libraries, a significant increase in the amount of liver-associated phage was observed only in the $4^{th}$ selection round (Table 1). This suggested a low incidence of liver-targeting phage clones in the original libraries. The percentage of infectious library phage recovered from perfused livers in the first round of selections with 13-mer and 8-mer libraries (~1%, Table 1) was roughly the same as observed previously for phage 20-6 that does not target liver (Sokoloff, Wong et al. 2003). This indicated that the library phage was unlikely to react with natural antibodies and/or complement, which typically leads to significant phage accumulation in liver Kupffer cells soon after injection (Pasqualini and Ruoslahti 1996; Sokoloff, Wong et al. 2003). Selection experiments conducted with immunodeficient Rag-1 mice that lack both T-cell and B compartments showed a similar phage yield dynamic, corroborating the view that the presence of the intact immune system in ICR mice did not have a significant effect on phage survival, clearance, and its cellular recognition.

Twenty-seven clones from the 7-mer selection were tested individually for liver targeting (Table 2). Fourteen clones showed low targeting efficiency, with <8% of input phage associated with liver, four clones targeted liver with medium efficiency (8-20%), and 9 clones exhibited high targeting efficiency (>20%). The phage uptake efficiency correlated with the net positive charge of selected residues. Thus the average charge of peptides with low targeting efficiency was +0.18 while the charge of peptide with medium and high targeting efficiency was +1.9 and 2.5, respectively (Table 2). It should be noted, however, that charge is not an absolute indicator of hepatocyte or liver targeting efficiency, as can be seen by the fact that some strong liver targeters have a charge of +1.5, while some moderate targeters have a charge of +2.

TABLE 1

Phage yields in selections for liver-specific peptides

| Selection round | Library | | |
|---|---|---|---|
| | 7-mer | 13-mer | 8-mer |
| 1 | 3.5 ± 0.6* | 1.1 ± 0.2 | 0.75 ± 0.5 |
| 2 | 16.2 ± 0.2* | 2.5 ± 0.5 | 2.4 ± 1.3 |
| 3 | 14 ± 1.6 | 2 ± 0.0 | 1.6 ± 0.4 |
| 4 | 28.7 ± 3.9 | 4.8 ± 1.3 | 2.8 ± 0.7 |
| 5 | 62 ± 5.7 | 26.6 ± 0.8 | 16.3 ± 2.0 |
| 6 | 74.2 ± 3.2 | 45.6 ± 4.3 | 35.1 ± 1.1 |
| 7 | 52.1 ± 12.3 | 59.6 ± 3.2 | 46.7 ± 4.0 |

Data are shown as mean ± SD for 3 mice.
*High values were apparently caused by incomplete liver perfusion as judged from some remaining liver coloration indicative of the presence of blood.

Clones with moderate and high targeting efficiency were further analyzed for their distribution in the liver (Table 2). Most of these clones were localized to liver sinusoids and, based on their staining, were likely to be present either in the space of Disse or at the vascular surface of endothelial cells (FIG. 3, d-f). The staining patterns produced by these clones were different from the patterns observed for both hepatocyte-specific phage 20-6F, which does not accumulate in sinusoids (FIG. 4, a and b; (Sokoloff, Wong et al. 2003)), and Kupffer-associated phage IL-1m (described below), which gives a characteristic scattered-clustering pattern (Sokoloff, Wong et al. 2003; see also FIG. 4c). Three clones were primarily associated with hepatocytes (FIG. 3, a-c), showing a general distribution pattern similar to that observed for clone 20-6F (FIG. 4, a and b).

The distribution of clones 1-18, 1-19, 1-21, and 2-38 were determined by analyzing phage accumulation in brain, kidney, lung, muscle and spleen. 30 minutes after phage injection, perfusion was performed and phage titers determined for each organ. None of these organs accumulated more than 1.4% of injected phage. The vast majority of phage that did not accumulate in the liver remained in the blood. This suggests that these selected clones target liver, but no other organs, efficiently.

The targeting properties of clone 1-21 (Table 2, "#"), chosen as a typical representative of clones targeting sinusoids (FIG. 3, d-f), were characterized in more detail using clone IL-1m, described earlier as "IL-1 mutated" (Sokoloff, Wong et al. 2003), as a comparison standard. When injected into mice, clone IL-1m is rapidly sequestered by Kupffer cells as a result of its reactivity with natural IgM and complement (FIG. 4c; (Sokoloff, Wong et al. 2003)). As noted above, the continuous staining pattern observed for sinusoid-targeting clones in general and clone 1-21 in particular was very different from the scattered-clustering pattern produced by IL-1m (FIG. 4, e and c, respectively). The limited role played by Kupffer cells in the uptake of clone 1-21 was corroborated by injecting this phage into clodronate-treated mice that had functionally inactive Kupffer cells (Schiedner, Hertel et al. 2003). With phage measured by a plaque assay, the clodronate treatment strongly reduced the liver uptake of phage IL-1m from 17±4.0 to 5±1.2% (p=0.001) while having no inhibitory effect on the uptake of hepatocyte-specific phage 20-6F, which rose from 56±4.5 to 76±9.4% (p=0.111; (Sokoloff, Wong et al. 2003)). Clone 1-21 responded to chlodronate treatment similarly to clone 20-6F, showing an increase in its liver uptake from 16±0.7 to 28±5.5 (p=0.312). This indicated that clone 1-21 was not associated to a significant degree with

TABLE 2

Peptides selected for liver targeting from the 7-mer library

| CLONE | 194 f | 197 b | 198 c | | 204 b | 205 c | | 208 f | 209/210 | 211 b | CHARGE* | UPTAKE %** | LOCATION *** | SEQ ID NO: |
|---|---|---|---|---|---|---|---|---|---|---|---|---|---|---|
| Wild type | T | NT | K | Q | WRDET | K | G | FR | D | EA | K | | | | (SEQ ID NO: 16) |
| Library | X | NT | X | X | WRDET | X | X | FR | X | E | X | | | | (SEQ ID NO: 17) |
| | | | | | | | | | | | | | LOW | | |
| 1-1 | E | Y | A | | K | K | | N | | S | +1 | 4.2 | | (SEQ ID NO: 18) |
| 1-4 | S | L | F | | V | G | | D | | T | −1 | 1.4 | | (SEQ ID NO: 19) |
| 1-9 | G | Y | Q | | G | L | | D | | L | −1 | 3.3 | | (SEQ ID NO: 20) |
| 1-20 | Q | L | K | | F | N | | H | | E | +0.5 | 1.8 | | (SEQ ID NO: 21) |
| 2-3 | D | Y | R | | S | N | | T | | L | 0 | 5.6 | | (SEQ ID NO: 22) |
| 2-4 | S | T | T | | S | T | | Y | | F | 0 | 5.3 | | (SEQ ID NO: 23) |
| 2-9 | V | K | G | | Y | K | | E | | I | +1 | 5.5 | | (SEQ ID NO: 24) |
| 2-14 | Y | R | S | | E | L | | H | | F | +0.5 | 2.6 | | (SEQ ID NO: 25) |
| 2-20 | A | I | K | | F | I | | E | | V | 0 | 3.6 | | (SEQ ID NO: 26) |
| 2-23 | A | R | R | | Y | I | | T | | S | +2 | 2.5 | | (SEQ ID NO: 27) |
| 2-26 | K | Q | E | | Y | F | | D | | N | −1 | 1.9 | | (SEQ ID NO: 28) |
| 2-29 | L | V | I | | E | G | | R | | V | 0 | 2.8 | | (SEQ ID NO: 29) |
| 2-34 | R | W | A | | F | N | | S | | L | +1 | 3.3 | | (SEQ ID NO: 30) |
| 32-37 | S | H | E | | L | A | | V | | S | −0.5 | 2.5 | | (SEQ ID NO: 31) |
| | | | | | | | | | | | | | MEDIUM | | |
| 1-6 | E | R | L | | Y | K | | K | | Y | +2 | 16.6 | H + S | (SEQ ID NO: 32) |
| 1-18# | L | R | R | | K | I | | V | | E | +2 | 9.6 | H | (SEQ ID NO: 33) |
| 1-19# | G | Q | K | | L | R | | Y | | T | +2 | 12.7 | S | (SEQ ID NO: 34) |
| 2-41 | K | R | E | | K | H | | E | | I | +1.5 | 8 | S | (SEQ ID NO: 35) |
| | | | | | | | | | | | | | HIGH | | |
| 1-5# | A | N | Q | | I | R | | S | | R | +2 | 21.9 | S | (SEQ ID NO: 36) |
| 1-10# | T | R | R | | Q | T | | I | | K | +3 | 30.9 | H | (SEQ ID NO: 37) |
| 1-17 | G | V | H | | K | R | | E | | I | +1.5 | 26.6 | H + S | (SEG ID NO: 38) |
| 1-21# | T | K | Q | | M | R | | K | | S | +3 | 44.4 | S | (SEQ ID NO: 39) |
| 2-11 | S | R | A | | N | K | | I | | K | +3 | 59.9 | H + S | (SEQ ID NO: 40) |
| 2-15 | S | A | T | | H | H | | S | | K | +2 | 54.3 | H + S | (SEQ ID NO: 41) |
| 2-22 | V | S | R | | K | H | | S | | A | +2.5 | 63.5 | H + S | (SEQ ID NO: 42) |
| 2-36 | Q | R | V | | L | V | | K | | K | +4 | 77.5 | H + S | (SEQ ID NO: 43) |
| 2-38# | K | T | H | | Q | N | | S | | R | +1.5 | 33 | H | (SEQ ID NO: 44) |

Variable residues are identified by their p17 and coiled-coil positions in the top rows.
K/R residues are in bold.
*The charge ascribed to a D/E, K/R and H residue was −1, +1, and +0.5.
**Liver uptake as a percentage of injected phage.
***H, hepatocytes; S, sinusoids.
Clones shown in FIG. 3.

Kupffer cells. The independence of clone 1-21 uptake of clodronate treatment was confirmed by immunohistochemistry. As shown in FIG. 4, the clodronate treatment had no significant effect on the liver distribution of clones 1-21 and 20-6F but virtually eliminated the accumulation by Kupffer cells of clone IL-1m. Given that all sinusoid-accumulated phage clones tested by immunohistochemistry produced staining patterns similar to that of clone 1-21, they were also likely to be associated with liver elements other than Kupffer cells. Electron microscopy with enhanced immunogold staining of phage further characterized the specific location of phage within the liver. While the staining procedure was difficult to adapt for visualization of intracellular phage, it was well suited for detection of extracellular phage bound to the cell surface. The vast majority of phage particles was present in the space of Disse and associated with microvilli of hepatocytes (FIG. 5b). No phage was bound to the luminal surface of endothelial cells although occasional phage particles might have been associated with the basal surface of endothelial cells.

Approximately 50-fold enrichment for liver-associated phage was observed in the $7^{th}$ selection round with the 13-mer library (Table 1). Forty clones were sequenced and sixteen of these clones, displaying collectively fifteen unique sequences, fell into four consensus groups (Table 3, outlined). The remaining twenty four clones displayed non-homologous sequences. Five individual clones from this selection were tested for liver accumulation using a plaque assay and found to target the liver with an efficiency ranging from 45 to 85% (Table 3, "*"). Six clones from this selection that lacked K residues in variable positions were analyzed further because their cognate synthetic peptides would be more amenable for conjugation to delivery vehicles using amino groups (Table 3, "**"). Using immunohistochemistry, all of them were found to accumulate in liver sinusoid regions (data not shown).

Approximately 60-fold enrichment for liver-associated phage was observed in the $7^{th}$ round of selection with the 8-mer library that was devoid of K, W, E, M and Q residues (Table 1, round 7). Notably, a high proportion of selected peptides were mutated at invariant positions, which could possibly be a compensation for the reduced diversity of residues at the variable positions (Table 4, underlined residues). The mutation of invariant residues suggests that significant liver targeting by peptide sequences requires a certain minimal level of peptide complexity. The targeting properties of individual clones from this selection were not analyzed.

TABLE 3

Peptides selected for liver targeting from the 13-mer library

| CLONE | 194 (f) | 195 (g) | 196 (a) | 197 (b) | 198 (c) | | 204 (b) | 205 (c) | 206 (d) | 207 (e) | 208 (f) | 209 (g) | 210 (a) | 211 (b) | SEQ ID NO: |
|---|---|---|---|---|---|---|---|---|---|---|---|---|---|---|---|
| Wild type | T | N | T | K | Q | WRDET | K | G | F | R | D | E | A | K | (SEQ ID NO: 16) |
| Library | X | X | X | X | X | WRDET | X | X | X | X | X | X | X | X | (SEQ ID NO: 45) |
| 2-2*/ | R | N | T | A | R | | Q | T | F | R | T | E | A | R** | (SEQ ID NO: 46) |
| 2-13 | R | N | T | R | V | | S | T | F | R | N | E | A | R | (SEQ ID NO: 47) |
| 2-36 | L | N | T | K | R | | T | S | F | R | Q | E | A | R | (SEQ ID NO: 48) |
| 2-3 | S | N | M | S | R | | S | R | L | V | R | R | L | E | (SEQ ID NO: 49) |
| 2-8*/** | T | Q | M | E | N | | S | R | A | S | R | R | S | L | (SEQ ID NO: 50) |
| 2-44 | T | Q | M | E | N | | S | R | A | S | R | R | S | L | (SEQ ID NO: 51) |
| 2-15 | G | S | I | R | K | | V | I | L | S | K | R | S | S | (SEQ ID NO: 52) |
| 2-47 | S | R | I | Q | A | | E | I | S | S | R | R | S | S | (SEQ ID NO: 53) |
| 2-45 | V | Q | M | Q | L | | L | L | S | R | S | R | S | L | (SEQ ID NO: 54) |
| 2-37 | Q | A | I | A | L | | A | V | S | R | N | K | S | L | (SEQ ID NO: 55) |
| 2-34 | D | V | V | K | G | | Y | E | S | R | D | K | C | R | (SEQ ID NO: 56) |
| 2-6* | L | N | T | G | R | | K | M | F | R | R | E | A | M | (SEQ ID NO: 57) |
| 2-18 | L | N | T | G | R | | D | S | F | R | R | E | A | R | (SEQ ID NO: 58) |
| 2-22 | S | N | T | N | K | | T | L | F | R | R | E | A | R | (SEQ ID NO: 59) |
| 2-27 | Y | N | T | N | M | | S | R | F | R | R | E | A | G | (SEQ ID NO: 60) |
| 2-29 | I | N | T | N | V | | G | R | F | R | K | E | A | L | (SEQ ID NO: 61) |

TABLE 3-continued

Peptides selected for liver targeting from the 13-mer library

| | | | | | | | | | | | | | | |
|---|---|---|---|---|---|---|---|---|---|---|---|---|---|---|
| 2-4 | M | E | V | R | L | I | P | V | L | R | R** | I | L | (SEQ ID NO: 62) |
| 2-10 | R | K | S | E | M | A | A | N | Y | R | R | I | S | (SEQ ID NO: 63) |
| 2-25 | E | G | V | N | L | S | R | N | C | K | R | A | L | (SEQ ID NO: 64) |
| 2-39 | T | L | I | S | R | N | L | L | Y | K | R | Q | H | (SEQ ID NO: 65) |
| 2-41 | A | G | I | H | G | L | G | A | L | K | R | V | V | (SEQ ID NO: 66) |
| 2-12 | A | H | C | R | T | Q | K | T | T | E | R | L | R | (SEQ ID NO: 67) |
| 2-20 | E | G | I | R | T | A | V | A | S | V | R | A | R** | (SEQ ID NO: 68) |
| 2-21 | V | Q | V | S | T | I | V | S | T | T | R | T | R** | (SEQ ID NO: 69) |
| 2-35 | R | G | V | A | A | A | T | F | T | Y | R | S | R | (SEQ ID NO: 70) |
| 2-26 | R | A | S | L | I | A | R | Y | T | K | S | G | R | (SEQ ID NO: 71) |
| 2-30 | T | N | T | K | Q | I | K | A | A | R | L | I | R | (SEQ ID NO: 72) |
| 2-32 | Q | A | L | A | E | H | E | I | S | R | L | S | R** | (SEQ ID NO: 73) |
| 2-49 | E | G | V | S | K | I | S | L | V | K | Y | V | R | (SEQ ID NO: 74) |
| 2-5 | E | M | I | G | R | L | P | R | L | R | S | V | L | (SEQ ID NO: 75) |
| 2-9* | K | R | V | I | G | Q | R | L | T | S | R | I | M | (SEQ ID NO: 76) |
| 2-14 | K | V | I | S | V | R | S | S | F | L | R | T | S | (SEQ ID NO: 77) |
| 2-16 | A | A | V | S | S | K | L | F | L | T | R | S | Q | (SEQ ID NO: 78) |
| 2-19 | I | S | C | Q | V | R | V | N | T | Q | R | S | S | (SEQ ID NO: 79) |
| 2-33 | K | A | M | G | K | Q | I | L | A | Q | R | A | H | (SEQ ID NO: 80) |
| 2-1* | Y | S | M | N | A | I | K | N | A | I | S | S | R | (SEQ ID NO: 81) |
| 2-24 | H | T | I | G | L | L | K | S | V | A | S | S | R | (SEQ ID NO: 82) |
| 2-38 | V | Y | V | K | E | H | T | R | F | V | S | T | R | (SEQ ID NO: 83) |
| 2-42 | N | N | Q | R | L | K | T | W | F | G | M | S | R | (SEQ ID NO: 84) |
| 2-43 | K | M | V | H | G | V | T | S | S | T | L | T | R | (SEQ ID NO: 85) |

Notes to Table 3:
The outlined are homology groups. Variable residues are identified by their p17 and coiled-coil positions in the top rows. K/R residues are in bold. *Clones tested for liver accumulation. **Clones analyzed for liver distribution.

TABLE 4

Peptides selected for liver targeting from the 8-mer library

| | PEPTIDE STRUCTURE | | | | | | | | | | | |
|---|---|---|---|---|---|---|---|---|---|---|---|---|
| CLONE | 186 (e) | 190 (b) | 191 (c) | | 197 (b) | 198 (c) | | 204 (b) | 205 (c) | | 214 (e) | SEQ ID NO: |
| Wild type | K | NES | S | T | NATNT | K | Q | WRDET | K | G | FRDEAKRF | K | (SEQ ID NO: 86) |
| Library | X | NES | X | X | NATNT | X | X | WRDET | X | X | FRDEARRF | X | (SEQ ID NO: 87) |
| 3-2 | K | | S | T | NA<u>RSV</u> | K | T | | A | R | LHQ<u>R</u>ILRF | K | (SEQ ID NO: 88) |
| 3-3 | K | | S | T | <u>A</u>ATNT | K | Q | WRD<u>K</u>T | K | G | | K | (SEQ ID NO: 89) |
| 3-7 | R | | S | T | <u>A</u>ATNT | K | Q | WRD<u>K</u>T | K | G | | K | (SEQ ID NO: 90) |
| 3-8 | R | | S | T | <u>A</u>ATNT | K | Q | WRD<u>K</u>T | K | G | | K | (SEQ ID NO: 91) |
| 3-4 | K | | S | T | | K | Q | | | L | FRDEA<u>K</u>RF | K | (SEQ ID NO: 92) |
| 3-9 | K | | S | T | | K | Q | | | L | FRDEA<u>K</u>RF | K | (SEQ ID NO: 93) |
| 3-10 | K | | S | T | | K | Q | | | S | FRDEA<u>K</u>RF | K | (SEQ ID NO: 94) |
| 3-6 | H | | R | Y | | H | S | | I | A | | S | (SEQ ID NO: 95) |
| 3-12 | Y | | S | S | | Y | N | | R | T | | F | (SEQ ID NO: 96) |
| 3-13 | K | | S | T | | K | Q | | K | G | | G | (SEQ ID NO: 97) |
| 3-16 | K | | S | T | | R | V | | Q | K | FR<u>K</u>EALRF | K | (SEQ ID NO: 98) |
| 3-18 | K | | S | T | | G | R | | D | S | FR<u>R</u>EARRF | K | (SEQ ID NO: 99) |

The underlined are mutated invariant residues. Variable residues are identified by their p17 and coiled-coil positions in the top rows. K/R residues are in bold.

Evaluation of Putative Liver Targeting Sequences

The utility of the p17 display in testing putative liver targeting peptide determinants was tested using as a model the ApoB sequence comprising residues 3147-3157. There is evidence that the ApoB determinant, which is recognized by hepatic subendothelial HSPG and LDL receptor and mediates ApoB sequestration by hepatocytes, consists of two distant heparin-binding sequences, comprising residues 3147-3157 and 3359-3369, that are brought into proximity by a disulfide bond (Olsson, Camejo et al. 1997). It has been demonstrated that mutations in sequence 3359-3369 abolish the binding activity of ApoB (Boren, Olin et al. 1998); however, the contribution of sequence 3147-3157 to the ApoB binding has not been characterized in detail. We tested the liver-targeting activity of this sequence by displaying it in p17 and examining the accumulation of the "ApoB" phage in the liver. These experiments showed that the presence of sequence 3144-3159 in p17 was sufficient to target the phage to liver sinusoids and mediate its uptake by hepatocytes (FIG. 2a). Notably, a distinct difference, correlating with the known biological properties of ApoB and ApoE, was observed between the liver distribution patterns shown by phage displaying ApoE and ApoB sequences. The ApoE phage was observed exclusively in sinusoids (FIG. 2b), where it is expected to accumulate based on the model that free ApoE primarily resides in the space of Disse where it is attached to HSPG (Shimano, Namba et al. 1994). The ApoB phage, on the other hand, was observed both in sinusoid areas and within hepatocytes (FIG.

2a), which is also expected given that ApoB is constitutively present within lipoproteins and interacts with HSPG and LDL receptor on a competitive basis (Boren, Olin et al. 1998).

In summary, the above examples have demonstrated that the phage display system of the present invention is able to identify a variety of peptides with different targeting preferences. Several selected peptides targeted hepatocytes with subsequent phage internalization and were thus of interest as potential ligands for therapeutic delivery vehicles.

These experiments have also shown that hepatocyte-targeting sequences are quite common among selected peptides and, therefore, a large pool of such sequences may be readily generated as starting material for identifying the most effective hepatocyte-specific ligands with the lowest immunogenicity. The majority of selected peptides guide phage into liver sinusoid regions, indicating that these peptides may be recognized by receptors present on both parenchymal and non-parenchymal liver cells, as well as by extracellular matrix components present in the space of Disse. The experiments with chlodronate-treated mice have shown that sinusoidal-targeting clones mostly react with liver components other than Kupffer cells.

While further studies are required to determine the exact molecular and cellular location of these clones, the electron microscopy experiments have demonstrated that sinusoid-targeting phage is present in the space of Disse and mostly found in proximity of hepatocyte microvilli. This indicates that two different types of hepatocyte-specific peptides, presumably reacting with different types of cellular receptors, have been selected: one type includes peptides that target hepatocytes but fail to mediate productive phage internalization, and the other type represents peptides that enable both of these functions.

Besides finding new liver-specific peptide ligands, the p17 display system of the present invention is well suited for testing peptide sequences that have been implicated in liver targeting by the use of conventional biochemical techniques. The experiments conducted with the HSPG- and LDL receptor-binding peptide sequence derived from Apo E showed that the "ApoE" phage accumulated in liver sinusoid regions in accord with the previous biochemical studies (Shimano, Namba et al. 1994).

Similar experiments conducted with a less characterized ApoB sequence, thought to be a constituent of the bipartite HSPG- and LDL-reactive determinant (ApoB residues 3147-3157; (Olsson, Camejo et al. 1997)), showed that the presence of this sequence in p17 (residues 3144-3159) was sufficient to target the phage to liver sinusoid regions and mediate its uptake by hepatocytes. This result is at variance with the demonstration that the mutation of Apo B sequence 3359-3369 alone, with sequence 3144-3159 kept intact, disrupts Apo B interactions with HSPG and the LDL receptor (Boren, Olin et al. 1998). One possible explanation for this discrepancy would be a long-range effect of mutations in sequence 3359-3369 on the recognition of sequence 3144-3159, which might be promoted by the spatial proximity of these sequences. Another explanation is the presence in phage of several accessible copies of this sequence, versus just one copy in ApoB, which could enhance the avidity of peptide-hepatocyte interactions. Overall, the results from these experiments suggest that sequence 3144-3159 may potentially play a more significant role in the functional activity of ApoB than suggested by the results of mutational analysis (Boren, Olin et al. 1998).

These results illustrate an important utility of the p17 display system. Given that most proteins and viruses have multiple and redundant targeting domains, mutation and deletion analysis is somewhat limited in its ability to evaluate the targeting properties of individual protein determinants. The phage display system of the present invention provides more of a "blank slate" for such evaluation and thus can provide important complementary information concerning targeting mechanisms.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

REFERENCES

Boren, J., K. Olin, I. Lee, A. Chait, T. N. Wight and T. L. Innerarity. 1998. Identification of the principal proteoglycan-binding site in LDL. A single-point mutation in apo-B100 severely affects proteoglycan interaction without affecting LDL receptor binding. *Journal of Clinical Investigation* 101(12): 2658-64.

Falciani, C., L. Lozzi, A. Pini and L. Bracci. 2005. Bioactive peptides from libraries. *Chemistry & Biology* 12(4): 417-26.

Molenaar, T. J., I. Michon, S. A. de Haas, T. J. van Berkel, J. Kuiper and E. A. Biessen. 2002. Uptake and processing of modified bacteriophage M13 in mice: implications for phage display. *Virology* 293(1): 182-91.

Novagen. 1999. T7 Select System Manual.

Olsson, U., G. Camejo, E. Hurt-Camejo, K. Elfsber, O. Wiklund and G. Bondjers. 1997. Possible functional interactions of apolipoprotein B-100 segments that associate with cell proteoglycans and the ApoB/E receptor. *Arteriosclerosis, Thrombosis, and Vascular Biology* 17(1): 149-55.

Pasqualini, R. and E. Ruoslahti. 1996. Organ targeting in vivo using phage display peptide libraries. *Nature* 380(6572): 364-6.

Schiedner, G., S. Hertel, M. Johnston, V. Dries, N. van Rooijen and S. Kochanek. 2003. Selective depletion or blockade of Kupffer cells leads to enhanced and prolonged hepatic transgene expression using high-capacity adenoviral vectors. *Molecular Therapy. the Journal of the American Society of Gene Therapy* 7(1): 35-43.

Shimano, H., Y. Namba, J. Ohsuga, M. Kawamura, K. Yamamoto, M. Shimada, T. Gotoda, K. Harada, Y. Yazaki and N. Yamada. 1994. Secretion-recapture process of apolipoprotein E in hepatic uptake of chylomicron remnants in transgenic mice. *Journal of Clinical Investigation* 93(5): 2215-23.

Sokoloff, A. V., I. Bock, G. Zhang, S. Hoffman, J. Dama, J. J. Ludtke, A. M. Cooke and J. A. Wolff. 2001. Specific recognition of protein carboxy-terminal sequences by natural IgM antibodies in normal serum. *Molecular Therapy: the Journal of the American Society of Gene Therapy* 3(6): 821-30.

Sokoloff, A. V., I. Bock, G. Zhang, M. G. Sebestyen and J. A. Wolff. 2000. The interactions of peptides with the innate immune system studied with use of T7 phage peptide display. *Molecular Therapy. the Journal of the American Society of Gene Therapy* 2(2): 131-9.

Sokoloff, A. V., M. Puckett, J. J. Ludtke and B. Fetterly. 2004. Sequence-specific binding of normal serum IgM to exposed protein C-termini. *Immunology*.

Sokoloff, A. V., S. C. Wong, J. J. Ludtke, M. G. Sebestyen, V. M. Subbotin, G. Zhang, T. Budker, M. Bachhuber, Y. Sumita and J. A. Wolff. 2003. A new peptide ligand that targets particles and heterologous proteins to hepatocytes in vivo. *Molecular Therapy. the Journal of the American Society of Gene Therapy.*

Son, M., S. J. Hayes and P. Serwer. 1988. Concatemerization and packaging of bacteriophage T7 DNA in vitro: determination of the concatemers' length and appearance kinetics by use of rotating gel electrophoresis. *Virology* 162(1): 38-46.

Son, M., S. J. Hayes and P. Serwer. 1989. Optimization of the in vitro packaging efficiency of bacteriophage T7 DNA: effects of neutral polymers. *Gene* 82(2): 321-5.

Steven, A. C., B. L. Trus, J. V. Maizel, M. Unser, D. A. Parry, J. S. Wall, J. F. Hainfeld and F. W. Studier. 1988. Molecular substructure of a viral receptor-recognition protein. The gp17 tail-fiber of bacteriophage T7. *Journal of Molecular Biology* 200(2): 351-65.

Trepel, M., W. Arap and R. Pasqualini. 2002. In vivo phage display and vascular heterogeneity: implications for targeted medicine. *Current Opinion in Chemical Biology* 6(3): 399-404.

Weisgraber, K. H. and S. C. Rall, Jr. 1987. Human apolipoprotein B-100 heparin-binding sites. *Journal of Biological Chemistry* 262(23): 11097-103.

Weisgraber, K. H., S. C. Rall, Jr., R. W. Mahley, R. W. Milne, Y. L. Marcel and J. T. Sparrow. 1986. Human apolipoprotein E. Determination of the heparin binding sites of apolipoprotein E3. *Journal of Biological Chemistry* 261(5): 2068-76.

Wisse, E., R. B. De Zanger, K. Charels, P. Van Der Smissen and R. S. McCuskey. 1985. The liver sieve: considerations concerning the structure and function of endothelial fenestrae, the sinusoidal wall and the space of Disse. *Hepatology* 5(4): 683-92.

Wong, S. C., D. Wakefield, J. Klein, S. D. Monahan, D. B. Rozema, D. L. Lewis, L. Higgs, J. J. Ludtke, A. V. Sokoloff and J. A. Wolff. 2006. Hepatocyte Targeting of Nucleic Acid Complexes and Liposomes by a T7 Phage p17 Peptide. *Molecular Pharmaceutics* in press.

Wu, J., M. H. Nantz and M. A. Zern. 2002. Targeting hepatocytes for drug and gene delivery: emerging novel approaches and applications. *Frontiers in Bioscience* 7: d717-25.

Zou, J., M. T. Dickerson, N. K. Owen, L. A. Landon and S. L. Deutscher. 2004. Biodistribution of filamentous phage peptide libraries in mice. *Molecular Biology Reports* 31(2): 121-9.

---

We claim:

1. A bacteriophage T7 display vector for expressing and displaying a first exogenous peptide encoded by a first exogenous polynucleotide, wherein the bacteriophage T7 display vector comprises a first coding sequence which encodes a bacteriophage T7 tail fiber protein p17, and wherein the first coding sequence comprises the nucleotide sequence of SEQ ID NO: 12 or SEQ ID NO: 13 and contains a first cloning site for insertion of the first exogenous polynucleotide sequence.

2. The bacteriophage T7 display vector according to claim 1, which further comprises a second coding sequence which encodes a T7 capsid protein p10B and contains a second cloning site for insertion of a second exogenous polynucleotide encoding a second exogenous peptide, wherein the T7 capsid protein p10B comprises the amino acid sequence of SEQ ID NO: 10 or SEQ ID NO: 11.

3. The bacteriophage T7 display vector of claim 1, which further comprises a second coding sequence which encodes a truncated T7 capsid protein p10B and contains a second cloning site for insertion of a second exogenous polynucleotide encoding a second exogenous peptide, wherein the truncated T7 capsid protein p10B comprises the amino acid sequence of positions 1-27 of SEQ ID NO: 10, or the amino acid sequence of SEQ ID NO: 11.

4. The bacteriophage T7 display vector of claim 3, wherein the first or second exogenous peptide comprises at least 7 amino acid residues.

5. The bacteriophage T7 display vector of claim 4, wherein the first or second exogenous peptide comprises not more than 19 amino acid residues.

6. The bacteriophage T7 display vector of claim 3, further comprising wild-type T7 protein p17 regulatory signals.

7. The bacteriophage T7 display vector of claim 6, wherein the wild-type capsid T7 protein p17 regulatory signals comprise a promoter, or a translation initiation signal, or both.

8. The bacteriophage T7 display vector of claim 7, further comprising a wild type p17 terminator.

9. The bacteriophage T7 display vector according to claim 3, wherein the second cloning site is contained in the coding sequence for the truncated T7 capsid protein p10B and the exogenous nucleotide sequence is inserted at the C terminus of the truncated T7 capsid protein p10B, or in frame internally of the truncated T7 capsid protein p10B.

10. A cell containing a bacteriophage T7 display vector of claim 1.

* * * * *